(12) United States Patent
Squitieri

(10) Patent No.: US 11,801,183 B2
(45) Date of Patent: Oct. 31, 2023

(54) APPROACHES TO DETERMINING HEALTH OF A LIVING BODY THROUGH ANALYSIS OF THE PRESSURE OF INFLATABLE CHAMBERS OF A PRESSURE-MITIGATION DEVICE

(71) Applicant: TurnCare, Inc., Palo Alto, CA (US)

(72) Inventor: Rafael Paolo Squitieri, Wilton, CT (US)

(73) Assignee: TurnCare, Inc., Palo Alto, CA (US)

( * ) Notice: Subject to any disclaimer, the term of this patent is extended or adjusted under 35 U.S.C. 154(b) by 0 days.

(21) Appl. No.: 17/362,504

(22) Filed: Jun. 29, 2021

(65) Prior Publication Data

US 2021/0361501 A1 Nov. 25, 2021

Related U.S. Application Data

(63) Continuation of application No. 17/236,955, filed on Apr. 21, 2021.

(60) Provisional application No. 63/013,074, filed on Apr. 21, 2020.

(51) Int. Cl.
| | | |
|---|---|---|
| *A61G 7/057* | (2006.01) | |
| *G16H 40/63* | (2018.01) | |
| *A61B 5/00* | (2006.01) | |
| *A61B 5/0205* | (2006.01) | |
| *G08B 21/04* | (2006.01) | |

(52) U.S. Cl.
CPC ........ *A61G 7/05769* (2013.01); *A61B 5/0002* (2013.01); *A61B 5/0004* (2013.01); *A61B 5/0015* (2013.01); *A61B 5/0205* (2013.01); *A61B 5/447* (2013.01); *A61B 5/746* (2013.01); *A61B 5/747* (2013.01); *A61G 7/05746* (2013.01); *G16H 40/63* (2018.01); *A61B 5/6887* (2013.01); *A61G 2203/34* (2013.01); *G08B 21/0461* (2013.01)

(58) Field of Classification Search
CPC ..... A61G 7/05769; G16H 4/63; A61B 5/0002
USPC ........................................................ 600/301
See application file for complete search history.

(56) References Cited

U.S. PATENT DOCUMENTS

| | | | |
|---|---|---|---|
| 5,216,768 | A | 6/1993 | Bodine et al. |
| 5,325,551 | A | 7/1994 | Tappel et al. |
| 2003/0046762 | A1 | 3/2003 | Stolpmann |
| 2004/0201487 | A1 | 10/2004 | Benson et al. |
| 2005/0172405 | A1 | 8/2005 | Menkedick et al. |

(Continued)

*Primary Examiner* — Scott Luan
(74) *Attorney, Agent, or Firm* — Perkins Coie LLP; Andrew T. Pettit

(57) ABSTRACT

Introduced here are pressure-mitigation systems able to mitigate the pressure applied to a human body by the surface of an object. A system can include a pressure-mitigation device with chambers whose pressure can be varied by a controller that regulates the flow of fluid produced by a pump. The controller may be deployed as part of a closed loop system that autonomously infers information related to the health of a patient based on data related to the pressure of these chambers. For example, the data may be examined to determine whether the values indicate the patient is properly situated. A notification may be presented responsive to determining that the patient is not situated on the pressure-mitigation device, the patient has been improperly situated on the pressure-mitigation device for a certain amount of time, etc. Thus, real-time feedback may be provided to those responsible for monitoring the patient.

19 Claims, 23 Drawing Sheets

(56) References Cited

U.S. PATENT DOCUMENTS

| | | | |
|---|---|---|---|
| 2008/0060138 A1* | 3/2008 | Price | A61B 5/447 |
| | | | 5/713 |
| 2010/0001864 A1 | 1/2010 | Obrien et al. | |
| 2010/0064443 A1 | 3/2010 | Lee | |
| 2010/0071137 A1 | 3/2010 | Doehler et al. | |
| 2014/0320290 A1 | 10/2014 | Reeder et al. | |
| 2015/0008710 A1 | 1/2015 | Young et al. | |
| 2016/0302729 A1 | 10/2016 | Starr et al. | |
| 2020/0268163 A1 | 8/2020 | Duvert et al. | |

* cited by examiner

1000

1001

Determine that a pressure-mitigation device has been connected to a controller

1002

Identify a pattern associated with the pressure-mitigation device

1003

Cause chambers of the pressure-mitigation device to be inflated in accordance with the pattern

Determine that a pressure-mitigation device has been connected to a controller

1102

Identify a pattern corresponding to the pressure-mitigation device

1103

Cause chambers of the pressure-mitigation device to be inflated in accordance with the pattern

1104

Acquire pressure data representative of the values of electrical signals generated by transducer(s) mounted in the controller

1105

Examine the pressure data to identify movements, if any, of the human body situated on the pressure-mitigation device

Determine that a pressure-mitigation device has been connected to a controller

1302

Identify a pattern corresponding to the pressure-mitigation device

1303

Cause chambers of the pressure-mitigation device to be inflated in accordance with the pattern

1304

Acquire pressure data representative of the values of electrical signals generated by transducer(s) mounted in the controller

1305

Estimate a value for a characteristic of a human body based on the pressure data and/or information derived from the pressure data

1306

Transmit information related to the characteristic to a destination across a network

Obtain data indicative of the pressure of the chambers of a pressure-mitigation device that is presently deployed

1402

Examine the pressure data to infer a location, position, or orientation of the human body situated on the pressure-mitigation device

1403

Produce data that is representative of the location, position, or orientation of the human body

1404

Calculate a coverage metric indicative of the amount of time that the human body has been properly positioned on the pressure-mitigation device based on the pressure data, motion data, or any combination thereof

1405

Cause presentation of a notification that specifies the coverage metric or a recommendation based on the coverage metric

1501
Cause chambers of a pressure-mitigation device to be inflated or deflated to varying degrees in accordance with a programmed pattern

1502
Obtain data that indicates the pressure of at least some of the chambers of the pressure-mitigation device

1503
Examine the pressure data so as to establish a location of a human body with respect to the chambers

1504
Produce, based on the location, an output that indicates whether the human body is properly positioned on the pressure-mitigation device as required by a treatment regimen

1505
Transmit information related to the output to a destination across a network

Obtain data that indicates the pressure of each of multiple chambers of a pressure-mitigation device over an interval of time

1602

Parse the pressure data to discover a pattern of values that is indicative of a medical event experienced by a human body situated on the pressure-mitigation device

1603

Generate a notification responsive to a determination that the medical event occurred based on the discovery of the pattern of values

FIGURE 16

APPROACHES TO DETERMINING HEALTH OF A LIVING BODY THROUGH ANALYSIS OF THE PRESSURE OF INFLATABLE CHAMBERS OF A PRESSURE-MITIGATION DEVICE

CROSS-REFERENCE TO RELATED APPLICATIONS

This application is a continuation application of U.S. application Ser. No. 17/236,955, titled "Network-Enabled Systems for Mitigating Pressure Applied to a Living Body by an Underlying Surface" and filed on Apr. 21, 2021, which claims priority to U.S. Provisional Application No. 63/013,074, titled "Network-Enabled Systems for Mitigating Contact Pressure" and filed on Apr. 21, 2020, each of which is incorporated by reference herein in its entirety.

TECHNICAL FIELD

Various embodiments concern network-enabled apparatuses able to mitigate the pressure applied to a human body by the surface of an object.

BACKGROUND

Pressure injuries—sometimes referred to as "decubitus ulcers," "pressure ulcers," "pressure sores," or "bedsores"—may occur as a result of steady pressure being applied in one location along the surface of the human body for a prolonged period of time. Regions with bony prominences are especially susceptible to pressure injuries. Pressure injuries are most common in individuals who are completely immobilized (e.g., on an operating table, bed, or chair) or have impaired mobility. These individuals may be older, malnourished, or incontinent, all factors that predispose the human body to formation of pressure injuries.

These individuals are often not ambulatory, so they sit or lie for prolonged periods of time in the same position. Moreover, these individuals may be unable to reposition themselves to alleviate pressure. Consequently, pressure on the skin and underlying soft tissue may eventually result in inadequate blood flow to the area, a condition referred to as "ischemia," thereby resulting in damage to the skin or underlying soft tissue. Pressure injuries can take the form of a superficial injury to the skin or a deeper ulcer that exposes the underlying tissues and places the individual at risk for infection. The resulting infection may worsen, leading to sepsis or even death in some cases.

There are various technologies on the market that profess to prevent pressure injuries. However, these conventional technologies have many deficiencies. For instance, these conventional technologies are unable to control the spatial relationship between a human body and a support surface (or simply "surface") that applies pressure to the human body. Consequently, individuals that use these conventional technologies may still develop pressure injuries or suffer from related complications.

BRIEF DESCRIPTION OF THE DRAWINGS

FIG. 10 is a flow diagram of a process for varying the pressure in the chambers of a pressure-mitigation device that is positioned between a human body and a surface in accordance with embodiments of the present technology.

FIG. 11 is a flow diagram of a process for establishing movements of the human body situated on a pressure-mitigation device without placing any sensors in direct contact with the human body in accordance with embodiments of the present technology.

FIG. 13 is a flow diagram of a process for establishing a value for a characteristic of the human body situated on a pressure-mitigation device based on an analysis of data representative of the pressure of the chambers of the pressure-mitigation device.

FIG. 14 is a flow diagram of a process for producing a coverage metric that indicates whether the pressure-mitigation device is being operated in accordance with a treatment regimen (also referred to as a "treatment program").

FIG. 15 is a flow diagram of a process for establishing whether a pressure-mitigation device that is deployed beneath a human body is being used in compliance with a treatment regimen.

FIG. 16 is a flow diagram of a process for discovering occurrences of medical events through analysis of data related to the pressure of chambers of a pressure-mitigation device.

Figure 1A:
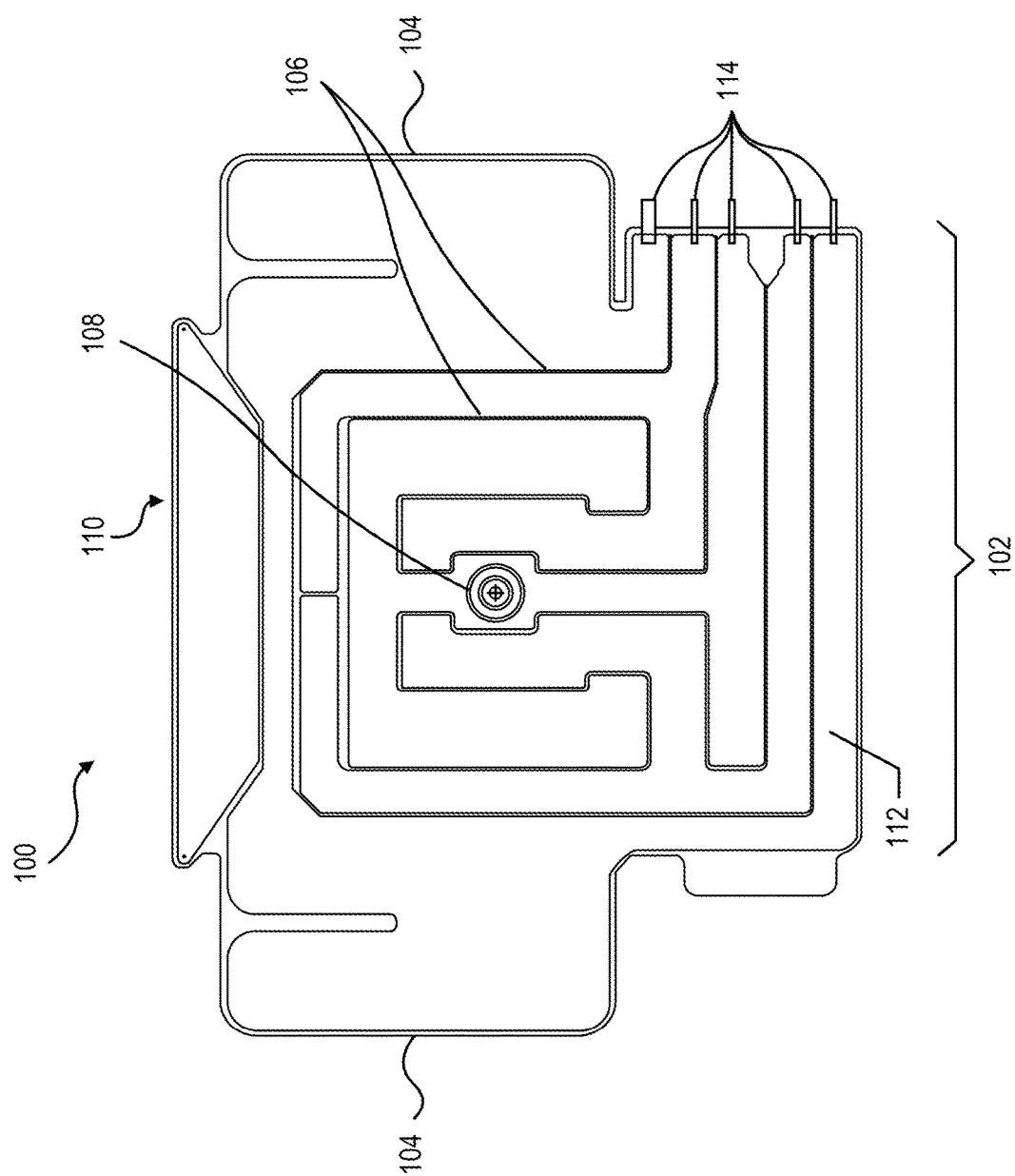
FIGS. 1A-B are top and bottom views, respectively, of a pressure-mitigation device able to relieve the pressure on an anatomical region applied by the surface of an elongated object in accordance with embodiments of the present technology.

Various features of the technologies described herein will become more apparent to those skilled in the art from a study of the Detailed Description in conjunction with the drawings. Embodiments are illustrated by way of example and not limitation in the drawings. While the drawings depict various embodiments for the purpose of illustration, those skilled in the art will recognize that alternative embodiments may be employed without departing from the principles of the technologies. Accordingly, while specific embodiments are shown in the drawings, the technology is amenable to various modifications

DETAILED DESCRIPTION

The term "pressure injury" refers to a localized region of damage to the skin and/or underlying tissue that results from contact pressure (or simply "pressure") on the corresponding anatomical region of the human body. Pressure injuries will often form over bony prominences, such as the skin and soft tissue overlying the sacrum, coccyx, heels, or hips. However, other sites may also be affected. For instance, pressure injuries may form on the elbows, knees, ankles, shoulders, abdomen, back, or cranium. Pressure injuries may develop when pressure is applied to the blood vessels in soft tissue in such a manner that blood flow to the soft tissue is at least partially obstructed (e.g., due to the pressure exceeding the capillary filling pressure), and ischemia results at the site when such obstruction occurs for an extended duration. Accordingly, pressure injuries are normally observed on individuals who are mobility impaired, immobilized, or sedentary for prolonged periods of times.

Once pressure injuries have formed, the healing process is normally slow. For example, when pressure is relieved from the site of a pressure injury, the body will rush blood (with proinflammatory mediators) to that region to perfuse the area with blood. The sudden reperfusion of the damaged (and previously ischemic) region has been shown to cause an inflammatory response, brought on by the proinflammatory mediators, that can actually worsen the pressure injury and prolong recovery. Moreover, in some cases, the proinflammatory mediators may spread through the blood stream beyond the site of the pressure injury to cause a systematic inflammatory response (also referred to as a "secondary inflammatory response"). The secondary inflammatory response caused by the proinflammatory mediators has been shown to exacerbate existing conditions and/or trigger new conditions, thereby slowing recovery. Recovery can also be prolonged by factors that are frequently associated with individuals who are prone to pressure injuries, such as old age, immobility, preexisting medical conditions (e.g., arteriosclerosis, diabetes, or infection), smoking, and medications (e.g., anti-inflammatory drugs). Inhibiting the formation of pressure injuries (and reducing the prevalence of proinflammatory mediators) can enhance and expedite many treatment processes, especially for those individuals whose mobility is impaired during treatment.

Introduced here, therefore, are network-enabled system able to mitigate the pressure applied to a living body by the surface of an object (also referred to as a "structure"). While embodiments may be described in the context of a human body, those skilled in the art will recognize that the network-enabled apparatuses could similarly be used in the context of, for example, animal bodies. A network-enabled system may comprise a controller device (or simply "controller") that is fluidically coupled to a pressure-mitigation device (also referred to as a "pressure-mitigation apparatus" or a "pressure-mitigation pad") that includes a series of selectively inflatable chambers (also referred to as "cells" or "compartments"). When a pressure-mitigation device is placed between a living body and a surface, the controller can continuously, intelligently, and autonomously circulate air through the chambers of the pressure-mitigation device. As further discussed below, the controller may cause the chambers to be selectively inflated, deflated, or any combination thereof.

By controllably varying the pressure in the series of chambers, the controller can move the main point of pressure applied by the surface to different anatomical regions of the living body. Said another way, the controller can move the main point of pressure across the surface of the living body. For example, the controller may cause the main point of pressure applied by the surface to be moved amongst a plurality of predetermined anatomical locations by sequentially varying the level of inflation of (and pressure in) predetermined subsets of chambers. Such an approach results in pressure gradients being created across the surface of the living body. In some embodiments, the controller controls the pressure of chambers located beneath specific anatomical locations for specific durations in order to move point(s) of pressure applied by the underlying surface around the anatomy in a precise manner such that specific portions of the anatomy (e.g., the tissue adjacent to bony prominences) do not experience direct pressure for an extended duration. The relocation of the pressure point(s) avoids vascular compression for sustained periods of time, inhibits ischemia, and reduces the incidence of pressure injuries.

The controller can include one or more transducers that are configured to generate an electrical signal based on the pressure of each chamber of the pressure-mitigation device. If, for example, the pressure-mitigation device includes three chambers interwoven together into a roughly rectangular pattern, the controller may include three transducers, each of which is operable to generate an electrical signal that is indicative of the pressure of a corresponding chamber. Accordingly, the controller may obtain pressure data that is representative of the values of the electrical signals generated by the transducers over time. As further discussed below, the controller can examine the pressure data to establish whether the pressure-mitigation device has been properly employed. For example, the controller may examine the pressure data to infer information regarding the length of the treatment session, movements of the living body, present location of the human body, etc. Additionally or alternatively, the controller can transmit the pressure data to another computing device (e.g., a computer server or mobile phone) that is responsible for inferring such information.

Rather than measure the pressure directly (e.g., with transducers), the pressure of chambers may be instead be inferred based on the rate at which fluid flows into the chambers in some embodiments. At a high level, the force applied to a given chamber by a living body can be inferred based on the rate at which fluid must flow into the given chamber to maintain a desired pressure. In a sense, the controller may be able to intelligently derive how much force is being applied to the pressure-mitigation device based on how difficult it is to maintain the pressure of the chambers. While embodiments may be described in the context of pressure data that based on electrical signals generated by transducers mounted in the controller, the embodiments are similarly applicable regardless of how that pressure data is generated. Accordingly, the controller may apply a heuristic, algorithm, or model that is programmed to estimate the force applied to the pressure-mitigation device a per-chamber basis based on the rate at which fluid must flow into those chambers to maintain a desired pressure, and the pressure data may be based on outputs produced by the heuristic, algorithm, or model.

Such an approach to monitoring the pressure of the chambers of the pressure-mitigation device allows the controller to be deployed as part of a closed loop system in which information related to the health state of the living body is autonomously inferred based on an analysis of the pressure data. For example, the pressure data may be examined (e.g., by the controller or the other computing device) to determine whether the values indicate the living body was properly arranged over the pressure-mitigation device. Notifications may be presented that indicate whether the living body was properly arranged over the pressure-mitigation device. For example, notifications may be presented to an administrator who is associated with a hospital in which the pressure-mitigation device is located, or notifications may be presented to a person (e.g., a healthcare professional or family member) who is responsible for managing treatment of the living body. Thus, feedback may be periodically or continually provided regarding whether the pressure-mitigation device is being properly used.

Embodiments may be described with reference to particular anatomical regions, treatment regimens, computing devices, networks, etc. However, those skilled in the art will recognize that the features are similarly applicable to other anatomical regions, treatment regimens, computing devices, networks, etc. As an example, embodiments may be described in the context of a pressure-mitigation device that is positioned adjacent to an anterior anatomical region of a person oriented in the prone position. However, aspects of those embodiments may apply to a pressure-mitigation device that is positioned adjacent to a posterior anatomical region of a person oriented in the supine position. As another example, although embodiments may be described in the context of a mobile application executing on a mobile phone that is communicatively coupled to a controller, the relevant features may be embodied in other types of computer programs and other types of computing devices.

While embodiments may be described in the context of machine-readable instructions, aspects of the technology can be implemented via hardware, firmware, or software. As an example, a controller may execute instructions for producing, based on pressure data, a metric that is indicative of the health of a living body based on the amount or type of movement exhibited by the living body while positioned on a pressure-mitigation device. As another example, a controller may execute instructions for generating, based on pressure data, notifications responsive to determining that a criterion (e.g., no movement for a predetermined interval of time, improper placement on the pressure-mitigation device) have been met.

These instructions may be executed as part of an instruction set that, when executed by a processor, causes the processor to examine data pertaining to the pressures of the chambers of a pressure-mitigation device arranged beneath a living body, infer movements and/or locations of the loving body over time based on the data, produce a compliance metric based on the inferred movements and/or locations, and then generate a notification that specifies the compliance metric. As mentioned above, the processor may be included in the controller or another computing device to which the controller is communicatively connected.

Terminology

References in this description to "an embodiment" or "one embodiment" means that the feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the terms "comprise," "comprising," and "comprised of" are to be construed in an inclusive sense rather than an exclusive or exhaustive sense (i.e., in the sense of "including but not limited to"). The term "based on" is also to be construed in an inclusive sense rather than an exclusive or exhaustive sense. Thus, unless otherwise noted, the term "based on" is intended to mean "based at least in part on."

The terms "connected," "coupled," or any variant thereof is intended to include any connection or coupling between two or more elements, either direct or indirect. The connection/coupling can be physical, logical, or a combination thereof. For example, objects may be electrically or communicatively coupled to one another despite not sharing a physical connection.

The term "module" may be used to refer broadly to software components, firmware components, hardware components, or any combination thereof. Modules are typically functional components that generate output(s) based on specified input(s). A computer program may include one or more modules. Thus, a computer program may include multiple modules responsible for completing different tasks or a single module responsible for completing all tasks.

When used in reference to a list of multiple items, the term "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Overview of Pressure-Mitigation Devices

A pressure-mitigation device includes a plurality of chambers (also referred to as "cells" or "compartments") into which air can flow. Each chamber may be associated with a discrete flow of air so that the pressure in the plurality of chambers can be varied as necessary. When placed on the surface of an object on which a human body rests, the pressure-mitigation device can vary the pressure on an anatomical region by controllably inflating chamber(s) and/ or deflating chamber(s) to create pressure gradients. Several examples of pressure-mitigation devices are described below with respect to FIGS. 1A-3. Unless otherwise noted, any features described with respect to one embodiment are equally applicable to other embodiments. Some features have only been described with respect to a single embodiment for the purpose of simplifying the present disclosure.

Figure 1B:
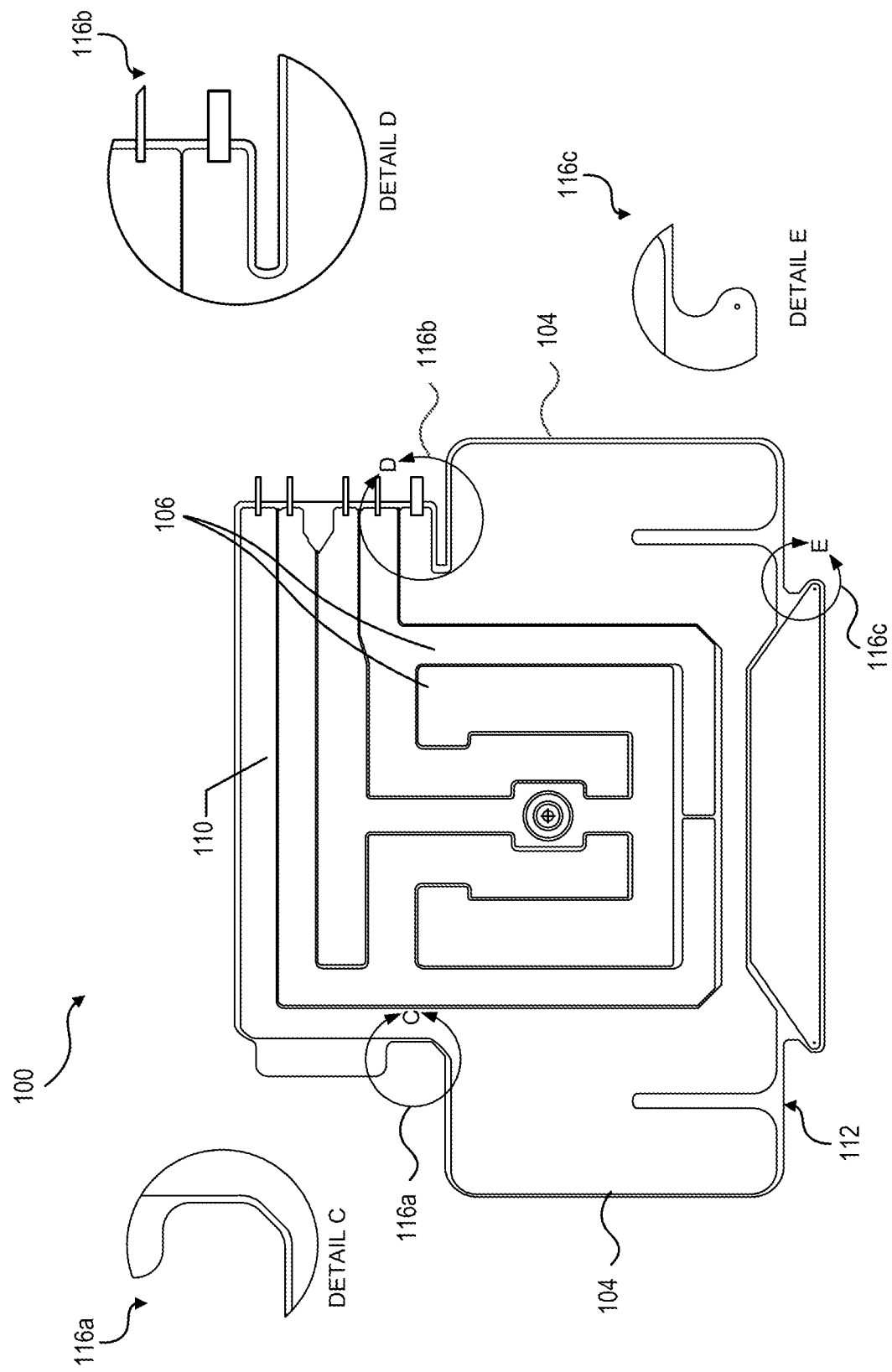

FIGS. 1A-B are top and bottom views, respectively, of a pressure-mitigation device 100 able to relieve the pressure on an anatomical region applied by the surface of an elongated object in accordance with embodiments of the present technology. While the pressure-mitigation device 100 may be described in the context of elongated objects, such as mattresses, stretchers, operating tables, and procedure tables, the pressure-mitigation device 100 could be deployed on non-elongated objects. In some embodiments, the pressure-mitigation device 100 is secured to a support surface using an attachment apparatus. In other embodiments, the pressure-mitigation device 100 is placed in direct contact with the surface without any attachment apparatus therebetween. For example, the pressure-mitigation device 100 may have a tacky substance deposited along at least a portion of its outer surface that allows it to temporarily adhere to the surface. Examples of tacky substances include latex, urethane, and silicone rubber.

As shown in FIG. 1A, the pressure-mitigation device 100 can include a central portion 102 (also referred to as a "contact portion") that is positioned alongside at least one side support 104. Here, a pair of side supports 104 are arranged on opposing sides of the central portion 102. However, some embodiments of the pressure-mitigation device 100 do not include any side supports. For example, the side support(s) 104 may be omitted when the individual is medically immobilized (e.g., under anesthesia, in a medically induced coma, etc.) and/or physically restrained by underlying object (e.g., by rails along the side of a bed, armrests along the side of a chair, etc.) or some other structure (e.g., physical restraints, casts, etc.).

The pressure-mitigation device 100 includes a series of chambers 106 whose pressure can be individually varied. In some embodiments, the series of chambers 106 are arranged in a geometric pattern designed to relieve pressure on specific anatomical region(s) of a human body. As noted above, when placed between the human body and a surface, the pressure-mitigation device 100 can vary the pressure on these specific anatomical region(s) by controllably inflating and/or deflating chamber(s).

In some embodiments, the series of chambers 106 are arranged such that pressure on a given anatomical region is mitigated when the given anatomical region is oriented over a target region 108 of the geometric pattern. As shown in FIGS. 1A-B, the target region 108 may be representative of a central point of the pressure-mitigation device 100 to appropriately position the anatomy of the human body with respect to the pressure-mitigation device 100. For example, the target region 108 may correspond to the center of the geometric pattern. However, the target region 108 may not necessarily be the central point of the pressure-mitigation device 100, particularly if the series of chambers 106 are positioned in a non-symmetric arrangement. The target region 108 may be visibly marked so that an individual can readily align the target region 108 with a corresponding anatomical region of the human body to be positioned thereon. Thus, the pressure-mitigation device 100 may include a visual element representative of the target region 108 to facilitate alignment with the corresponding anatomical region of the human body. The individual could be a healthcare professional, such as a physician, nurse, or personal care assistant (e.g., employed by a nursing home), or some other caregiver, such as a family member or friend of the patient. Alternatively, the individual could be the patient.

The pressure-mitigation device 100 can include a first portion 110 (also referred to as a "first layer" or "bottom layer") designed to face a surface and a second portion 112 (also referred to as a "second layer" or "top layer") designed to face the human body supported by the surface. In some embodiments, the pressure-mitigation device 100 is deployed such that the first portion 110 is directly adjacent to the surface. For example, the first portion 110 may have a tacky substance deposited along at least a portion of its exterior surface that facilitates temporarily adhesion to the support surface. In other embodiments, the pressure-mitigation device 100 is deployed such that the first portion 110 is directly adjacent to an attachment apparatus designed to help secure the pressure-mitigation device 100 to the support surface. The pressure-mitigation device 100 may be constructed of various materials, and the material(s) used in the construction of each component of the pressure-mitigation device 100 may be chosen based on the nature of the body contact, if any, to be experienced by the component. For example, because the second portion 112 will often be in direct contact with the skin, it may be comprised of a soft fabric or a breathable fabric (e.g., comprised of moisture-wicking materials or quick-drying materials, or having perforations). In some embodiments, an impervious lining (e.g., comprised of polyurethane) is secured to the inside of the second portion 112 to inhibit fluid (e.g., sweat) from entering the series of chambers 106. As another example, if the pressure-mitigation device 100 is designed for deployment beneath a cover (e.g., a bed sheet), then the second portion 112 may be comprised of a flexible, liquid-impervious material, such as polyurethane, polypropylene, silicone, or rubber. The first portion 110 may also be comprised of a flexible, liquid-impervious material.

The series of chambers 106 may be formed via interconnections between the first and second portions 110, 112. For example, the first and second portions 110, 112 may be bound directly to one another, or the first and second portions 110, 112 may be bound to one another via one or more intermediary layers. In the embodiment illustrated in FIGS. 1A-B, the pressure-mitigation device 100 includes an "M-shaped" chamber intertwined with two "C-shaped" chambers that face one another. Such an arrangement has been shown to effectively mitigate the pressure applied to the sacral region of a human body in the supine position by a support surface when the pressure in these chambers is alternated. The series of chambers 106 may be arranged differently if the pressure-mitigation device 100 is designed for an anatomical region other than the sacral region, or if the pressure-mitigation device 100 is to be used to support a human body in a non-supine position (e.g., a prone position or sitting position). Generally, the geometric pattern of chambers 106 is designed based on the internal anatomy (e.g., the muscles, bones, and vasculature) of the anatomical region on which pressure is to be relieved.

The user of the pressure-mitigation device 100 and/or the person responsible for monitoring the user may be responsible for actively orienting the anatomical region of the human body lengthwise over the target region 108 of the geometric pattern. If the pressure-mitigation device 100 includes one or more side supports 104, the side support(s) 104 may actively orient or guide the anatomical region of the human body laterally over the target region 108 of the geometric pattern. In some embodiments the side support(s)

104 are inflatable, while in other embodiments the side support(s) 104 are permanent structures that protrude from one or both lateral sides of the pressure-mitigation device 100. For example, at least a portion of each side support may be stuffed with cotton, latex, polyurethane foam, or any combination thereof.

As further described below with respect to FIGS. 6A-C, a controller can separately control the pressure in each chamber (as well as the side supports 104, if included) by providing a discrete airflow via one or more corresponding valves 114. In some embodiments, the valves 114 are permanently secured to the pressure-mitigation device 100 and designed to interface with tubing that can be readily detached (e.g., for easier transport, storage, etc.). Here, the pressure-mitigation device 100 includes five valves 114. Three valves are fluidically coupled to the series of chambers 106, and two valves are fluidically coupled to the side supports 104. Other embodiments of the pressure-mitigation device 100 may include more than five valves or less than five valves. For example, the pressure-mitigation device 100 may be designed such that a pair of side supports 104 are pressurized via a single airflow received via a single valve.

In some embodiments, the pressure-mitigation device 100 includes one or more design features 116a-c designed to facilitate securement of the pressure-mitigation device 100 to the surface of an object and/or an attachment apparatus. As illustrated in FIG. 1B, for example, the pressure-mitigation device 100 may include three design features 116a-c, each of which can be aligned with a corresponding structural feature that is accessible along the surface of the object or the attachment apparatus. For example, each design feature 116a-c may be designed to at least partially envelope a structural feature that protrudes upward. One example of such a structural feature is a rail that extends along the side of a bed. The design feature(s) 116a-c may also facilitate proper alignment of the pressure-mitigation device 100 with the surface of the object or the attachment apparatus.

Figure 2A:
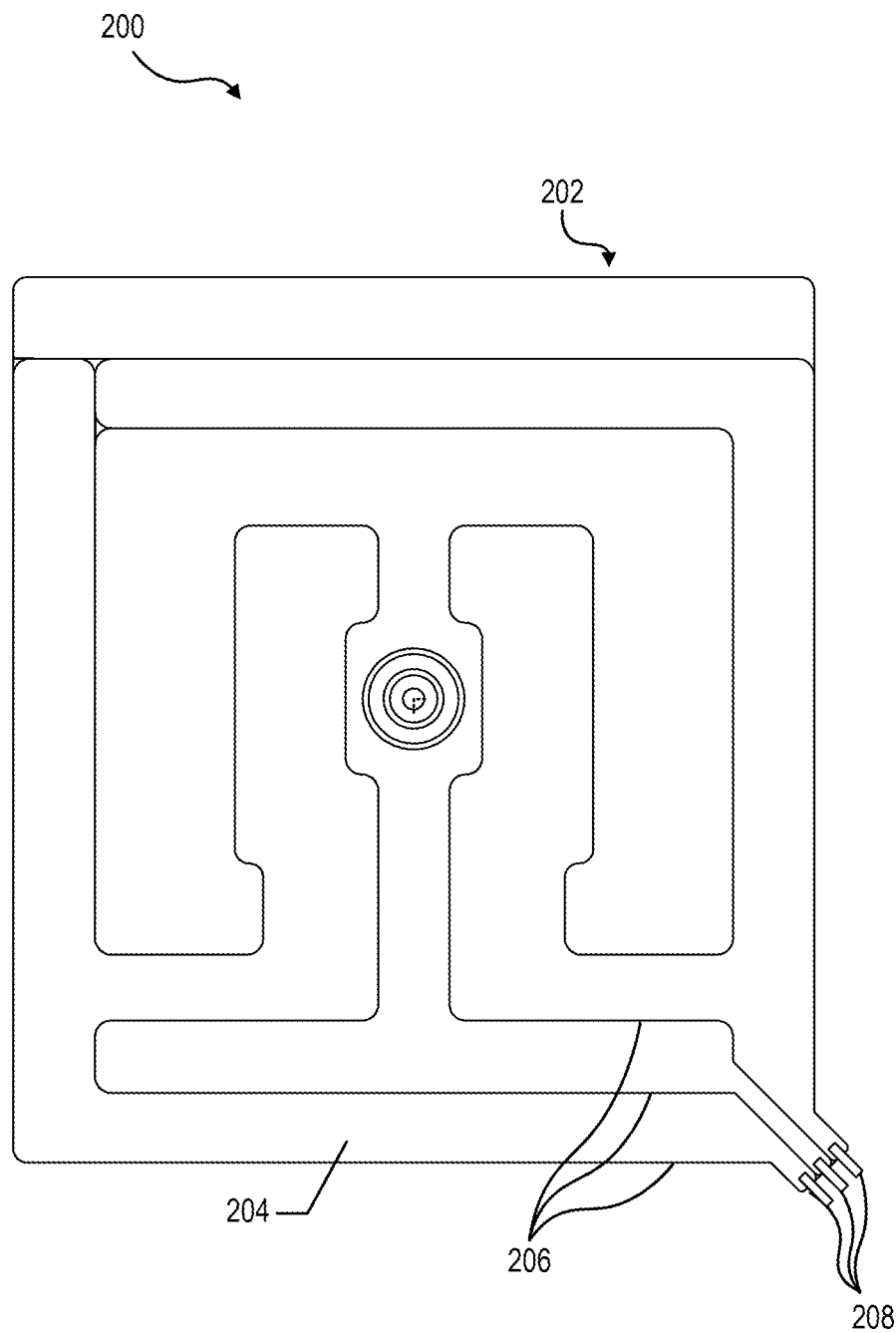
FIGS. 2A-B are top and bottom views, respectively, of a pressure-mitigation device configured in accordance with embodiments of the present technology.
Figure 2B:
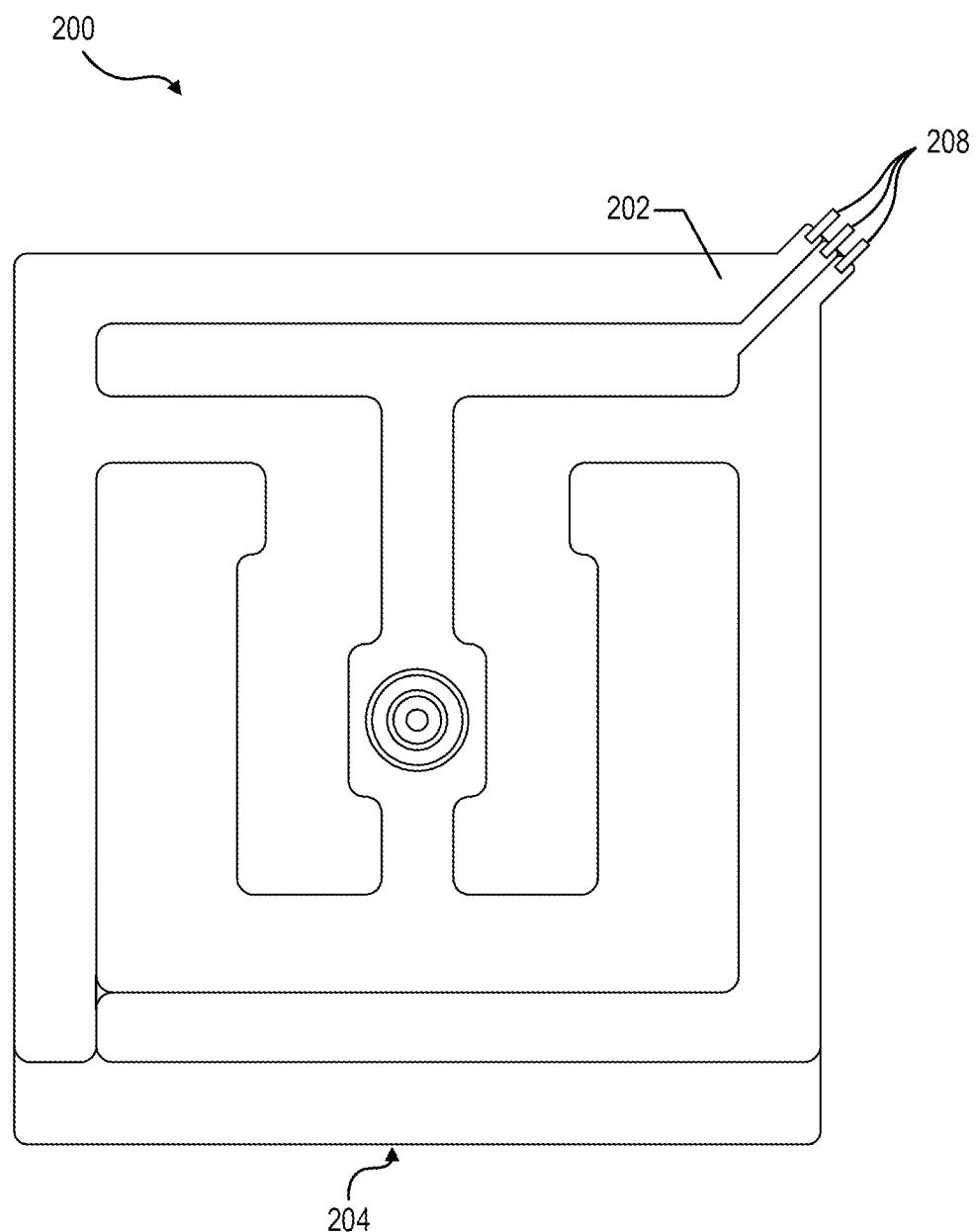

FIGS. 2A-B are top and bottom views, respectively, of a pressure-mitigation device 200 configured in accordance with embodiments of the present technology. The pressure-mitigation device 200 is generally used in conjunction with nonelongated objects that support individuals in a seated or partially erect position. Examples of nonelongated objects include chairs (e.g., office chairs, examination chairs, recliners, and wheelchairs) and the seats included in vehicles and airplanes. Accordingly, the pressure-mitigation device 200 may be positioned atop surfaces that have side supports integrated into the object itself (e.g., the side arms of a recliner or wheelchair). Note, however, that the pressure-mitigation device 200 could likewise be used in conjunction with elongated objects in a manner generally similar to the pressure-mitigation device 100 of FIGS. 1A-B.

In some embodiments, the pressure-mitigation device 200 is secured to a surface using an attachment apparatus. In other embodiments, the attachment apparatus is omitted such that the pressure-mitigation device 200 directly contacts the underlying surface. In such embodiments, the pressure-mitigation device 200 may have a tacky substance deposited along at least a portion of its outer surface that allows it to temporarily adhere to the surface.

The pressure-mitigation device 200 can include various features similar to the features of the pressure-mitigation device 100 described above with respect to FIGS. 1A-B. For example, the pressure-mitigation device 200 may include a first portion 202 (also referred to as a "first layer" or "bottom layer") designed to face the surface, a second portion 204 (also referred to as a "second layer" or "top layer") designed to face the human body supported by the surface, and a plurality of chambers 206 formed via interconnections between the first and second portions 202, 204. In this embodiment, the pressure-mitigation device 200 includes an "M-shaped" chamber intertwined with a backward "J-shaped" chamber and a backward "C-shaped" chamber. Varying the pressure in such an arrangement of chambers 206 has been shown to effectively mitigate the pressure applied by a surface to the gluteal and sacral regions of a human body in a seated position. These chambers may be intertwined to collectively form a square-shaped pattern. Pressure-mitigation devices designed for deployment on the surfaces of non-elongated objects may have substantially quadrilateral-shaped patterns of chambers, while pressure-mitigation devices designed for deployment on the surfaces of elongated objects may have substantially square-shaped patterns of chambers.

As further discussed below, the chambers 206 can be inflated and/or deflated in a predetermined pattern and to predetermined pressure levels. The individual chambers 206 may be inflated to higher pressure levels than the chambers 106 of the pressure-mitigation device 100 described with respect to FIGS. 1A-B because the human body being supported by the pressure-mitigation device 200 is in a seated position, thereby causing more pressure to be applied by the underlying surface than if the human body were in a supine or prone position. Further, unlike the pressure mitigation device 100 of FIGS. 1A-B, the pressure-mitigation device 200 of FIGS. 2A-B does not include side supports. As noted above, side supports may be omitted when the object on which the individual is situated (e.g., seated or reclined) already provides components that will laterally center the human body, as is often the case with nonelongated support surfaces. One example of such a component is the armrests along the side of a chair.

As further described below with respect to FIGS. 6A-C, a controller can control the pressure in each chamber 206 by providing a discrete airflow via one or more corresponding valves 208. Here, the pressure-mitigation device 200 includes three valves 208, and each of the three valves 208 corresponds to a single chamber 206. Other embodiments of the pressure-mitigation device 200 may include fewer than three valves or more than three valves, and each valve can be associated with one or more chambers to control inflation/deflation of those chamber(s). A single valve could be in fluid communication with two or more chambers. Further, a single chamber could be in fluid communication with two or more valves (e.g., one valve for inflation and another valve for deflation).

Figure 3:
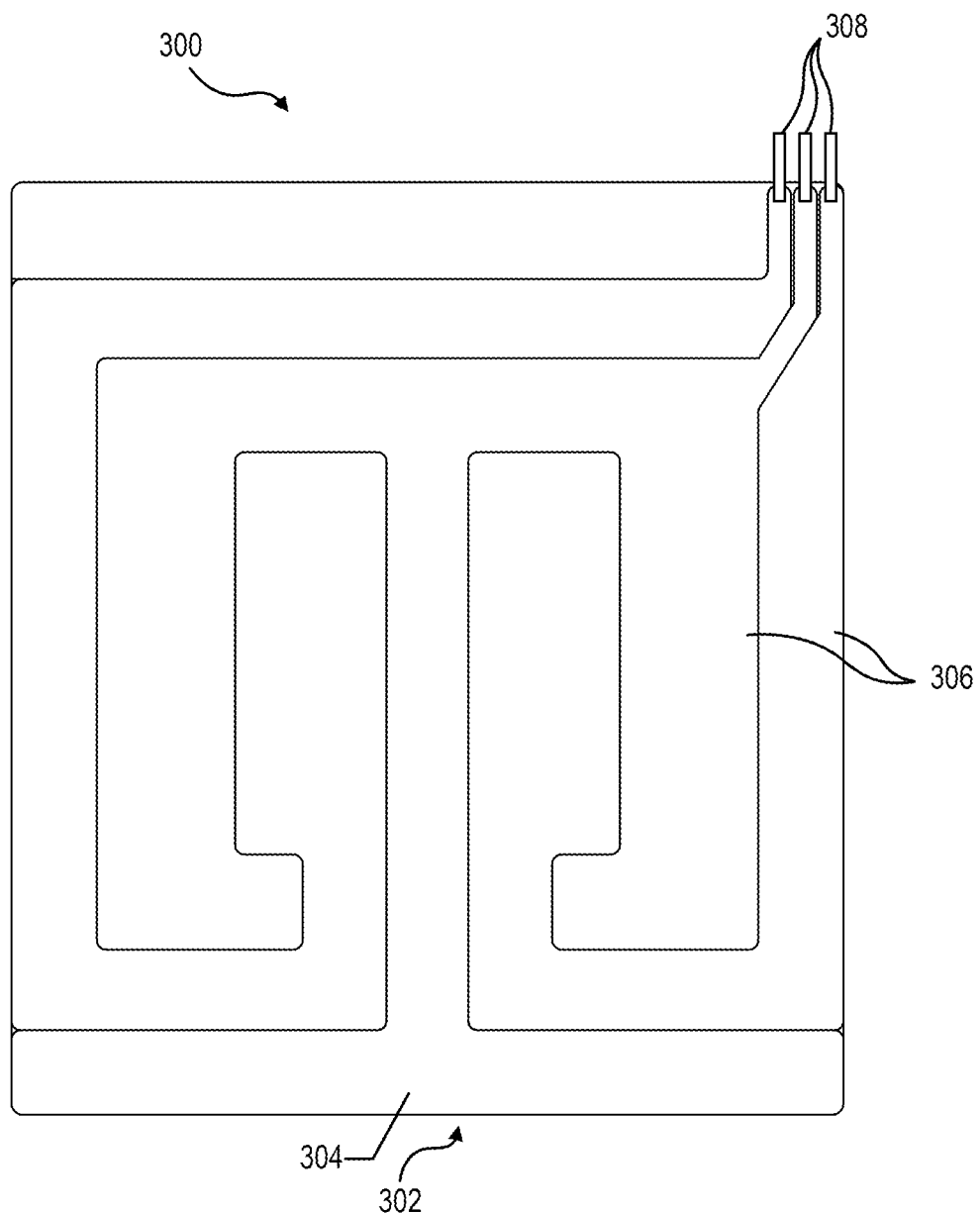
FIG. 3 is a top view of a pressure-mitigation device for relieving pressure on an anatomical region applied by a wheelchair in accordance with embodiments of the present technology.

FIG. 3 is a top view of a pressure-mitigation device 300 for relieving pressure on an anatomical region applied by a wheelchair in accordance with embodiments of the present technology. The pressure-mitigation device 300 can include features similar to the features of the pressure-mitigation device 200 of FIGS. 2A-B and the pressure-mitigation device 100 of FIGS. 1A-B described above. For example, the pressure-mitigation device 300 can include a first portion 302 (also referred to as a "first layer" or "bottom layer") designed to face the seat of the wheelchair, a second portion 304 (also referred to as a "second layer" or "top layer") designed to face the human body supported by the seat of the wheelchair, a series of chambers 306 formed by interconnections between the first and second portions 302, 304, and multiple valves 308 that control the flow of fluid into and/or out of the chambers 306. As can be seen in FIG. 3, the chambers 306 may be arranged similar to those shown in FIGS. 2A-B. Here, however, the pressure-mitigation device 300 is designed such that the valves 308 will be located near the backrest of the wheelchair. Such a design may allow the tubing connected to the valves 308 to be routed through a gap near, beneath, or in the backrest.

In some embodiments the first portion 302 is directly adjacent to the seat of the wheelchair, while in other embodiments the first portion 302 is directly adjacent to an attachment apparatus. As shown in FIG. 3, the pressure-mitigation device 300 may include an "M-shaped" chamber intertwined with a "U-shaped" chamber and a "C-shaped" chamber, which are inflated and deflated in accordance with a predetermined pattern to mitigate the pressure applied to the sacral region of a human body in a sitting position on the seat of a wheelchair. These chambers may be intertwined to collectively form a square-shaped pattern.

Figure 4:
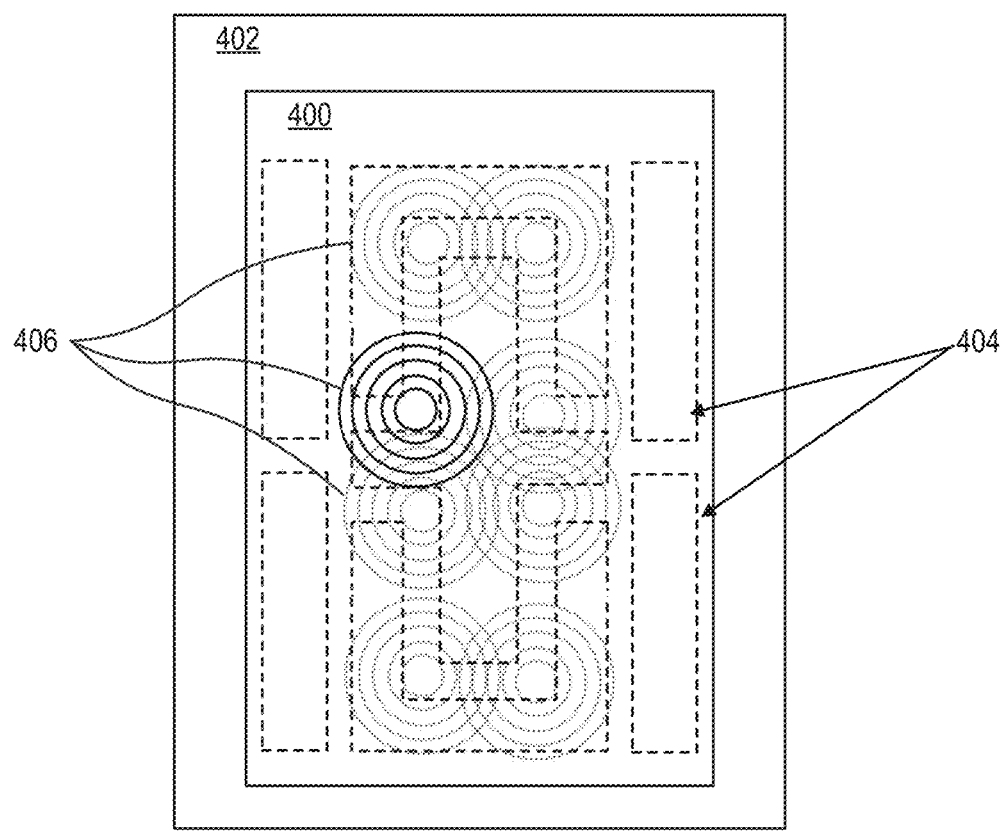
FIG. 4 is a partially schematic top view of a pressure-mitigation device illustrating how a pressure gradient can be created by varying pressure distributions to avoid ischemia in a mobility-impaired patient in accordance with embodiments of the present technology.

FIG. 4 is a partially schematic top view of a pressure-mitigation device 400 illustrating how a pressure gradient can be created by varying pressure distributions to avoid ischemia in a mobility-impaired patient in accordance with embodiments of the present technology. When a human body is supported by a surface 402 for an extended duration, pressure injuries may form in the tissue overlaying bony prominences, such as the skin overlying the sacrum, coccyx, heels, or hips. Generally, these bony prominences represent the locations at which the most pressure is applied by the surface 402 and, therefore, may be referred to as the "main pressure points" along the surface of the human body.

To prevent the formation of pressure injuries, healthy individuals periodically make minor positional adjustments (also known as "micro-adjustments") to shift the location of the main pressure point. However, individuals having impaired mobility often cannot make these micro-adjustments by themselves. Mobility impairment may be due to physical injury (e.g., a traumatic injury or a progressive injury), movement limitations (e.g., within a vehicle, on an aircraft, or in restraints), medical procedures (e.g., those requiring anesthesia), and/or other conditions that limit natural movement. For these mobility-impaired individuals, the pressure-mitigation device 400 can be used to shift the location of the main pressure point(s) on their behalf. That is, the pressure mitigation device 400 can create moving pressure gradients to avoid sustained, localized vascular compression and enhance tissue perfusion.

The pressure-mitigation device 400 can include a series of chambers 404 whose pressure can be individually varied. The chambers 404 may be formed by interconnections between the top and bottom layers of the pressure-mitigation device 400. The top layer may be comprised of a first material (e.g., a permeable, non-irritating material) configured for direct contact with a human body, while the bottom layer may be comprised of a second material (e.g., a non-permeable, gripping material) configured for direct contact with the surface 402. Generally, the first material is permeable to gasses (e.g., air) and/or liquids (e.g., water and sweat) to prevent buildup of fluids that may irritate the skin. Meanwhile, the second material may not be permeable to gasses or liquids to prevent soilage of the underlying object. Accordingly, air discharged into the chambers 404 may be able to slowly escape through the first material (e.g., naturally or via perforations) but not the second material, while liquids may be able to penetrate the first material (e.g., naturally or via perforations) but not the second material. Note, however, that the first material is generally be selected such that the top layer does not actually become saturated with liquid to reduce the likelihood of irritation. Instead, the top layer may allow liquid to pass therethrough into the cavities, from which the liquid can be subsequently discharged (e.g., as part of a cleaning process). The top layer and/or the bottom layer can be comprised of more than one material, such as a coated fabric or a stack of interconnected materials.

The pressure-mitigation device 400 may be designed such that inflation of at least some of the chambers 404 causes air to be continuously exchanged across the surface of the human body. Said another way, simultaneous inflation of at least some of the chambers 404 may provide a desiccating effect to inhibit generation and/or collection of moisture along the skin in a given anatomical region. In some embodiments, the pressure-mitigation device 400 is able to maintain airflow through the use of a porous material. For example, the top layer may be comprised of a biocompatible material through which air can flow (e.g., naturally or via perforations). In other embodiments, the pressure-mitigation device 400 is able to maintain airflow without the use of a porous material. For example, airflows can be created and/or permitted simply through varied pressurization of the chambers 404. This represents a new approach to microclimate management that is enabled by simultaneous inflation and deflation of the chambers 404. At a high level, each void formed beneath a human body due to deflation of at least one chamber can be thought of as a microclimate that cools and desiccates the corresponding portion of the anatomical region. Heat and humidity can lead to injury (e.g., further development of ulcers), so the cooling and desiccating effects may present some injuries due to inhabitation of moisture generation/collection along the skin in the anatomical region.

As discussed below with respect to FIG. 17, a pump (also referred to as a "pressure device") can be fluidically coupled to each chamber 404 (e.g., via a corresponding valve), while a controller can control the flow of fluid generated by the pump into each chamber 404 on an individual basis in accordance with a predetermined pattern. The controller can operate the series of chambers 404 in several different ways.

In some embodiments, the chambers 404 have a naturally deflated state, and the controller causes the pump to inflate at least one of the chambers 404 to shift the main pressure point along the anatomy of the user. For example, the pump may inflate at least one chamber 404 located directly beneath an anatomical region to momentarily apply contact pressure to that anatomical region and relieve contact pressure on the surrounding anatomical regions adjacent to the deflated chamber(s) 404. The controller may cause the pump to inflate two or more chambers 404 adjacent to an anatomical region to create a void beneath the anatomical region to shift the main pressure point at least momentarily away from the anatomical region.

In other embodiments, the chambers 404 have a naturally inflated state, and the controller causes the pump to deflate at least one of the chambers 404 to shift the main pressure point along the anatomy of the user. For example, the pump may deflate at least one chamber 404 located directly beneath an anatomical region, thereby forming a void beneath the anatomical region to momentarily relieve the contact pressure on the anatomical region.

Whether configured in a naturally deflated state or a naturally inflated state, the continuous or intermittent alteration of the inflation levels of the individual chambers 404 moves the location of the main pressure point across different portions of the human body. As shown in FIG. 4, for example, inflating and/or deflating the chambers 404 creates temporary contact regions 406 that move across the pressure-mitigation device 400 in a predetermined pattern, and thereby changing the location of the main pressure point(s)

on the human body for finite intervals of time. Thus, the pressure-mitigation device 400 can simulate the microadjustments made by healthy individuals to relieve stagnant pressure applied by the surface 402.

The series of chambers 404 may be arranged in an anatomy-specific pattern so that when the pressure of one or more chambers is altered, the contact pressure on a specific anatomical region of the human body is relieved (e.g., by shifting the main pressure point elsewhere). As an example, the main pressure point may be moved between eight different locations corresponding to the eight temporary contact regions 406 as shown in FIG. 4. In some embodiments the main pressure point shifts between these locations in a predictable manner (e.g., in a clockwise or counterclockwise pattern), while in other embodiments the main pressure point shifts between these locations in an unpredictable manner (e.g., in accordance with a random pattern, a semi-random pattern, and/or detected pressure levels). Those skilled in the art will recognize that the quantity and position of these temporary contact regions 406 may vary based on the arrangement of the chambers 404, the number of the chambers 404, the anatomical region supported by the pressure-mitigation device 400, the characteristics of the human body supported by the pressure mitigation device 400, and/or the condition of the user (e.g., whether the user is completely immobilized, partially immobilized, etc.).

As discussed above, the pressure-mitigation device 400 may not include side supports if the condition of the user (also referred to as the "patient" or "subject") would not benefit from the positioning assistance provided by the side supports. For example, side supports can be omitted when the patient is medically immobilized (e.g., under anesthesia, in a medically induced coma, etc.) and/or physically restrained on the underlying surface 402 (e.g., by rails along the side of a bed, arm rests on the side of a chair, restraints limiting movement of the patient, casts, etc.).

Figure 5A:
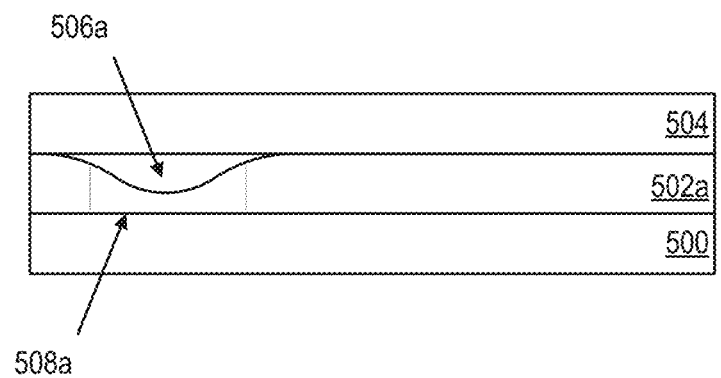
FIG. 5A is a partially schematic side view of a pressure-mitigation device for relieving pressure on a specific anatomical region by deflating chamber(s) in accordance with embodiments of the present technology.

FIG. 5A is a partially schematic side view of a pressure-mitigation device 502a for relieving pressure on a specific anatomical region by deflating chamber(s) in accordance with embodiments of the present technology. The pressure-mitigation device 502a can be positioned between the surface of an object 500 and a human body 504. Examples of objects 500 include beds, tables, and chairs. To relieve the pressure on a specific anatomical region of the human body 504, at least one chamber 508a of multiple chambers (collectively referred to as "chambers 508") proximate to the specific anatomical region is at least partially deflated to create a void 506a beneath the specific anatomical region. In such embodiments, the remaining chambers 508 may remain inflated. Thus, the pressure-mitigation device 502a may sequentially deflate chambers (or arrangements of multiple chambers) to relieve the pressure applied to the human body 504 by the surface of the object 500.

Figure 5B:
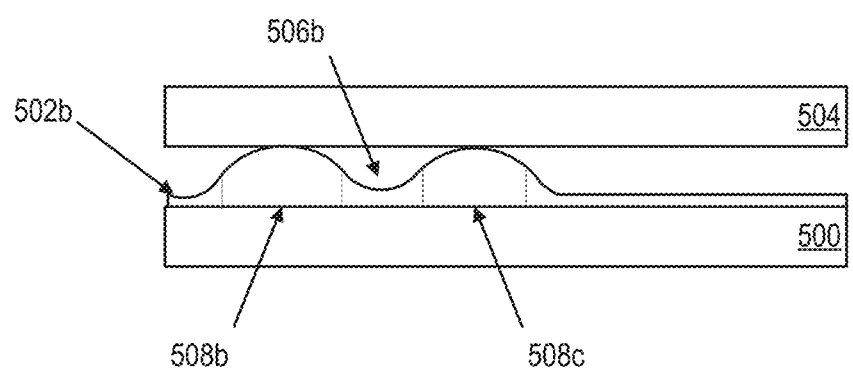
FIG. 5B is a partially schematic side view of a pressure-mitigation device for relieving pressure on a specific anatomical region by inflating chamber(s) in accordance with embodiments of the present technology.

FIG. 5B is a partially schematic side view of a pressure-mitigation device 502b for relieving pressure on a specific anatomical region by inflating chamber(s) in accordance with embodiments of the present technology. For example, to relieve the pressure on a specific anatomical region of the human body 504, the pressure-mitigation device 502b can inflate two chambers 508b and 508c disposed directly adjacent to the specific anatomical region to create a void 506b beneath the specific anatomical region. In such embodiments, the remaining chambers may remain partially or entirely deflated. Thus, the pressure-mitigation device 502b may sequentially inflate a chamber (or arrangements of multiple chambers) to relieve the pressure applied to the human body 504 by the surface of the object 500.

The pressure-mitigation devices 502a, 502b of FIGS. 5A-B are shown to be in direct contact with the contact surface 500. However, in some embodiments, an attachment apparatus is positioned between the pressure-mitigation devices 502a, 502b and the contact surface 500.

In some embodiments, the pressure-mitigation devices 502a, 502b of FIGS. 5A-B have the same configuration of chambers 508, and can operate in both a normally inflated state (described with respect to FIG. 5A) and a normally deflated state (described with respect to FIG. 5B) based on the selection of an operator (e.g., the user or some other person, such as a healthcare professional or family member). For example, the operator can use a controller to select a normally deflated mode such that the pressure-mitigation device operates as described with respect to FIG. 5B, and then change the mode of operation to a normally inflated mode such that the pressure-mitigation device operates as described with respect to FIG. 5A. Thus, the pressure-mitigation devices described herein can shift the location of the main pressure point by controllably inflating chambers, controllably deflating chambers, or a combination thereof.

Overview of Controller Devices

Figure 6A:
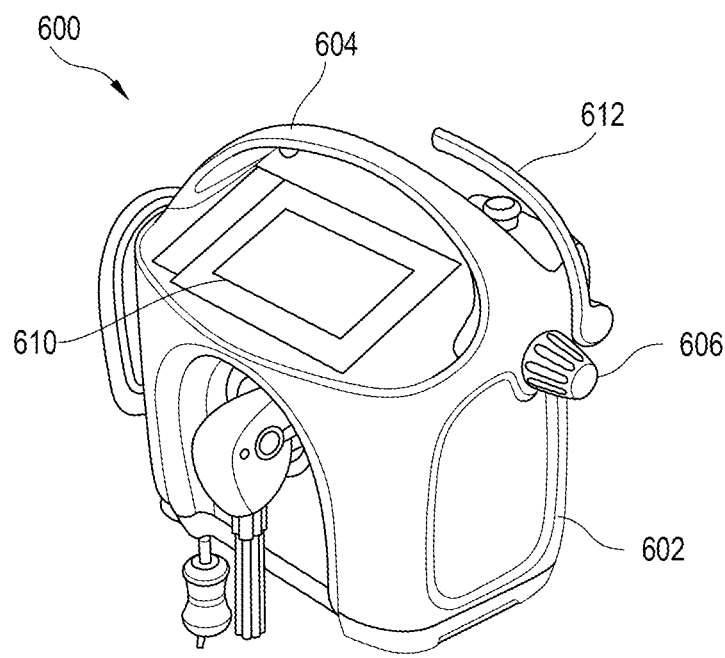
FIGS. 6A-C are isometric, front, and back views, respectively, of a controller device (also referred to as a "controller") that is responsible for controlling inflation and/or deflation of the chambers of a pressure-mitigation device in accordance with embodiments of the present technology.
Figure 6B:
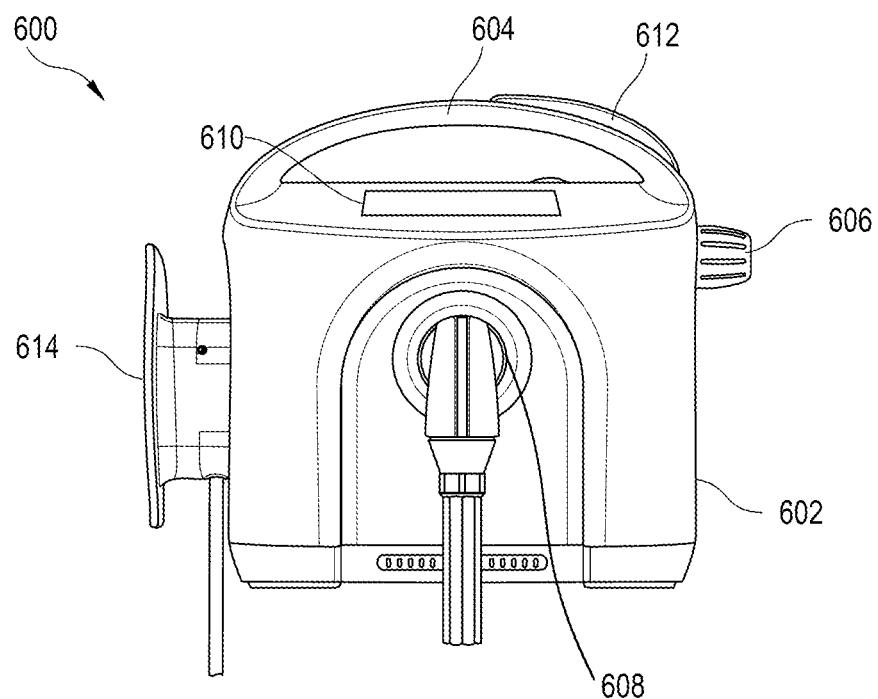
Figure 6C:
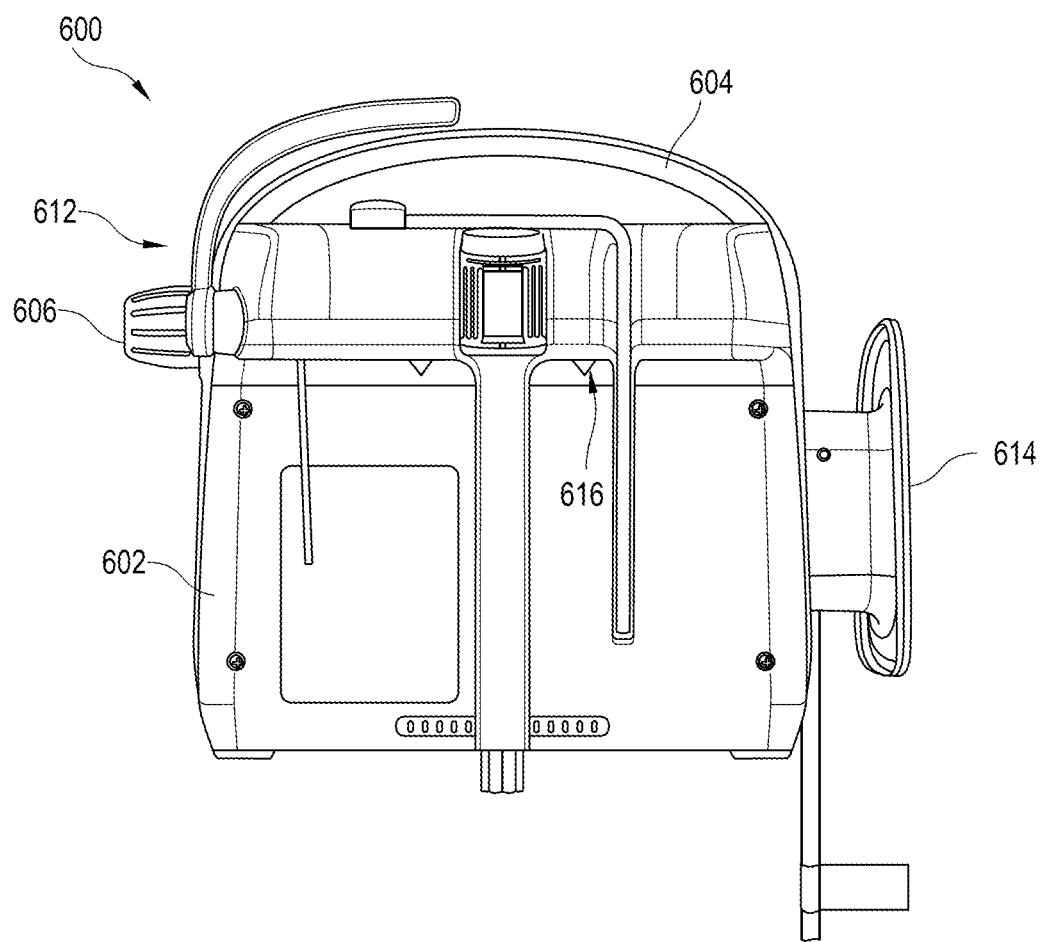

FIGS. 6A-C are isometric, front, and back views, respectively, of a controller device 600 (also referred to as a "controller") that is responsible for controlling inflation and/or deflation of the chambers of a pressure-mitigation device in accordance with embodiments of the present technology. For example, the controller 600 can be coupled to the pressure-mitigation devices 100, 200, 300 described above with respect to FIGS. 1A-3 to control the pressure within the chambers 106, 206, 306. The controller 600 can manage the pressure in each chamber of a pressure-mitigation device by controllably driving one or more pumps. In some embodiments, a single pump is fluidically connected to all the chambers such that the pump is responsible for directing fluid flow to and/or from multiple chambers. In other embodiments, the controller 600 is coupled to two or more pumps, each of which can be fluidically coupled to a single chamber to drive inflation/deflation of that chamber. In other embodiments, the controller 600 is coupled to at least one pump that is fluidically coupled to two or more chambers and/or at least one pump that is fluidically coupled to a single chamber. The pump(s) may reside within the housing of the controller 600 such that the system is easily transportable. Alternatively, the pump(s) may reside in a housing separate from the controller 600.

As shown in FIGS. 6A-C, the controller 600 can include a housing 602 in which internal components (e.g., those described below with respect to FIG. 7) reside and a handle 604 that is connected to the housing 602. In some embodiments the handle 604 is fixedly secured to the housing 602 in a predetermined orientation, while in other embodiments the handle 604 is pivotably secured to the housing 602. For example, the handle 604 may be rotatable about a hinge connected to the housing 602 between multiple positions. The hinge may be one of a pair of hinges connected to the housing 602 along opposing lateral sides. The handle 604 enables the controller 600 to be readily transported, for example, from a storage location to a deployment location (e.g., proximate a user positioned on a surface). Moreover, the handle 604 could be used to releasably attach the controller 600 to a structure. For example, the handle could be hooked on an intravenous (IV) pole (also referred to as an "IV stand" or "infusion stand").

In some embodiments, the controller 600 includes a retention mechanism 614 that is attached to, or integrated within, the housing 602. Cords (e.g., electrical cords), tubes, and/or other elongated structures associated with the system can be wrapped around or otherwise supported by the retention mechanism 614. Thus, the retention mechanism 614 may provide strain relief and retention of an electrical cord (also referred to as a "power cord"). In some embodiments, the retention mechanism 614 includes a flexible flange that can retain the plug of the electrical cord.

As further shown in FIGS. 6A-C, the controller 600 may include a connection mechanism 612 that allows the housing 602 to be securely, yet releasably, attached to a structure. Examples of structures include IV poles, mobile workstations (also referred to as "mobile carts" or "computer carts"), bedframes, rails, handles (e.g., of wheelchairs), and tables. The connection mechanism 612 may be used instead of, or in addition to, the handle 604 for mounting the controller 600 to the structure. In the illustrated embodiment, the connection mechanism 612 is a mounting hook that allows for single-hand operation and is adjustable to allow for attachment to mounting surfaces with various thicknesses. In some embodiments, the controller 600 includes an IV pole clamp 616 that eases attachment of the controller 600 to IV poles. The IV pole clamp 616 may be designed to enable quick securement, and the IV pole clamp 616 can be self-centering with the use of a single activation mechanism (e.g., knob or button).

In some embodiments, the housing 602 includes one or more input components 606 for providing instructions to the controller 600. The input component(s) 606 may include knobs (e.g., as shown in FIGS. 6A-C), dials, buttons, levers, and/or other actuation mechanisms. An operator can interact with the input component(s) 606 to alter the airflow provided to the pressure-mitigation device, discharge air from the pressure-mitigation device, or disconnect the controller 600 from the pressure-mitigation device (e.g., by disconnecting the controller 600 from tubing connected between the controller 600 and pressure-mitigation device).

As further discussed below, the controller 600 can be configured to inflate and/or deflate the chambers of a pressure-mitigation device in a predetermined pattern by managing the flow of fluid (e.g., air) produced by one or more pumps. In some embodiments the pump(s) reside in the housing 602 of the controller 600, while in other embodiments the controller 600 is fluidically connected to the pump(s). For example, the housing 602 may include a first fluid interface through which fluid is received from the pump(s) and a second fluid interface through which fluid is directed to the pressure-mitigation device. Multi-channel tubing may be connected to either of these fluid interfaces. For example, multi-channel tubing may be connected between the first fluid interface of the controller 600 and multiple pumps. As another example, multi-channel tubing may be connected between the second fluid interface of the controller 600 and multiple valves of the pressure-mitigation device. Here, the controller 600 includes a fluid interface 608 designed to interface with multi-channel tubing. In some embodiments the multi-channel tubing permits unidirectional fluid flow, while in other embodiments the multi-channel tubing permits bidirectional fluid flow. Thus, fluid returning from the pressure-mitigation device (e.g., as part of a discharge process) may travel back to the controller 600 through the second fluid interface. By controlling the exhaust of fluid returning from the pressure-mitigation device, the controller 600 can actively manage the noise created during use.

By monitoring the connection with the fluid interface 608, the controller 600 may be able to detect which type of pressure-mitigation device has been connected. Each type of pressure-mitigation device may include a different type of connector. For example, a pressure-mitigation device designed for elongated objects (e.g., the pressure-mitigation device 100 of FIGS. 1A-B) may include a first arrangement of magnets in its connector, while a pressure-mitigation device designed for non-elongated objects (e.g., the pressure-mitigation device of FIGS. 2A-B) may include a second arrangement of magnets in its connector. The controller 600 may include one or more sensors arranged near the fluid interface 608 that are able to detect whether magnets are located within a specified proximity. The controller 600 may automatically determine, based on which magnets have been detected by the sensor(s), which type of pressure-mitigation device is connected.

Pressure-mitigation devices may have different geometries, layouts, and/or dimensions suitable for various positions (e.g., supine, prone, sitting), various supporting objects (e.g., wheelchair, bed, recliner, surgical table), and/or various user characteristics (e.g., weight, size, ailment), and the controller 600 can be configured to automatically detect the type of pressure-mitigation device connected thereto. In some embodiments, the automatic detection is performed using other suitable identification mechanisms, such as the controller 600 reading a radio-frequency identification (RFID) tag or barcode on the pressure-mitigation device. Alternatively, the controller 600 may permit the operator to specify the type of pressure-mitigation device connected thereto. For example, the operator may be able to select, using an input component (e.g., input component 606), a type of pressure-mitigation device via a display 610. The controller 600 can be configured to dynamically alter the pattern for inflating and/or deflating chambers based on which type of pressure-mitigation device is connected.

As shown in FIGS. 6A-B, the controller 600 may include a display 610 for displaying information related to the pressure-mitigation device, the pattern of inflations/deflations, the patient, etc. For example, the display 610 may present an interface that specifies which type of pressure-mitigation device (e.g., the pressure-mitigation devices 100, 200, 300 of FIGS. 1A-3) is connected to the controller 600. Other display technologies could also be used to convey information to an operator of the controller 600. In some embodiments, the controller 600 includes a series of lights (e.g., light-emitting diodes) that are representative of different statuses to provide visual alerts to the operator or the user. For example, a status light may provide a green visual indication if the controller 600 is presently providing therapy, a yellow visual indication if the controller 600 has been paused (i.e., is in a pause mode), a red visual indication if the controller 600 has experienced an issue (e.g., non-compliance of patient, patient not detected) or requires maintenance (i.e., is in an alert mode), etc. These visual indications may dim upon the conclusion of a specified period of time or upon determining that the status has changed (e.g., the pause mode is no longer active).

In some embodiments, the controller 600 includes a rapid deflate function that allows an operator to rapidly deflate the pressure-mitigation device. The rapid deflate function may be designed such that the entire pressure-mitigation device is deflated or a portion (e.g., the side supports) of the pressure-mitigation device is deflated. This is a software solution that can be activated via the display 610 (e.g., when configured as a touch-enabled interface) and/or input components (e.g., tactile actuators such as buttons, switches, etc.) on the controller 600. This rapid deflation, in particular the deflation of the side supports, is expected to be beneficial to operators when there is a need for quick access to the user, such as to provide cardiopulmonary resuscitation (CPR).

In some embodiments, the controller 600 includes an audio output unit (also referred to as a "speaker") through which audio can be presented to nearby individuals. For example, instructions may be presented to the user to reposition herself, or instructions may be presented to a caregiver to adjust a setting. Moreover, the controller 600 may include an audio input unit (also referred to as a "microphone") that is capable of detecting speech uttered by nearby individuals. Together, the speaker and microphone may permit direct communications with individuals who are not located near the pressure-mitigation device. For example, if the user requests that a call be made (e.g., to a caregiver or emergency services), the controller 600 may initiate the call via a communication module and then facilitate the resulting conversation using the speaker and microphone. As another example, the controller 600 may be able to facilitate conversations between users and healthcare professionals who are not located near each other (e.g., where users are located in homes and healthcare professionals are located in healthcare facilities).

Figure 7:
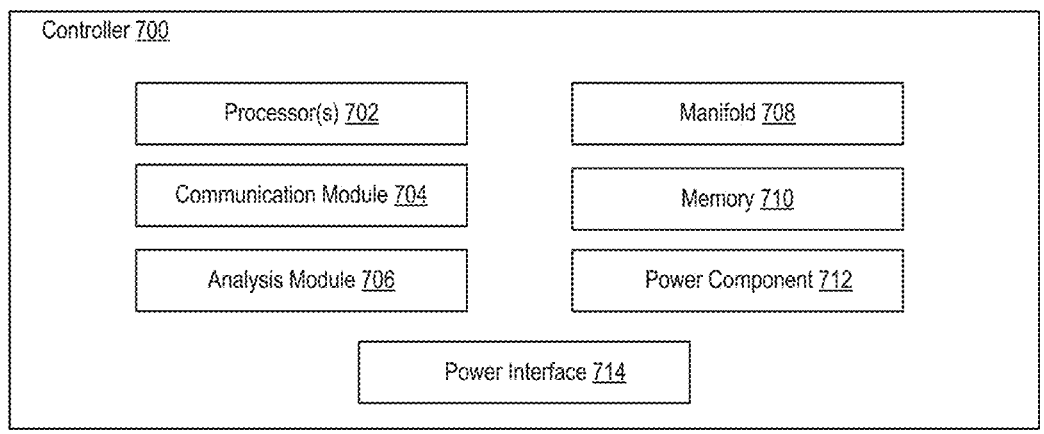
FIG. 7 is a block diagram illustrating components of a controller in accordance with embodiments of the present technology.

FIG. 7 is a block diagram illustrating components of a controller 700 in accordance with embodiments of the present technology. The controller 700 can include a processor 702, communication module 704, analysis module 706, manifold 708, memory 710, and/or power component 712 that is electrically coupled to a power interface 714. These components may reside within a housing (also referred to as a "structural body"), such as the housing 602 described above with respect to FIGS. 6A-C. In some embodiments, the controller 700 is incorporated into other component(s) of a pressure-mitigation system. For example, some components of the controller 700 may be incorporated into a computing device (e.g., a mobile phone or a mobile workstation) that is remotely coupled to a pressure-mitigation device. Embodiments of the controller 700 can include any subset of the components shown in FIG. 7, as well as additional components not illustrated here. For example, some embodiments of the controller 700 include a physical data interface through which data can be transmitted to another computing device. Examples of physical data interfaces include Ethernet ports, Universal Serial Bus (USB) ports, and proprietary ports.

The controller 700 may be connected to a pressure-mitigation device that includes a series of chambers whose pressure can be individually varied. When the pressure-mitigation device is placed between a human body and the surface of an object, the controller 700 can cause the pressure on an anatomical region of the human body to be varied by controllably inflating chamber(s), deflating chamber(s), or any combination thereof. Such action can be accomplished by the manifold 708, which controls the flow of fluid to the series of chambers of the pressure-mitigation device. The manifold 708 is further described with respect to FIGS. 8-9.

As further discussed below, transducers mounted in the manifold 708 can generate an electrical signal based on the pressure detected in each chamber of the pressure-mitigation device. Generally, each chamber is associated with a different fluid channel and a different transducer. Accordingly, if the manifold 708 is designed to facilitate the flow of fluid to a four-chamber pressure-mitigation device, the manifold 708 may include four fluid channels and four transducers. In some embodiments, the manifold 708 includes fewer than four fluid channels and/or transducers or more than four fluid channels and/or transducers. Pressure data representative of the values of the electrical signals generated by the transducers can be stored, at least temporarily, in the memory 710. As further discussed below, the manifold 708 may be driven based on a clock signal generated by a clock module (not shown). For example, the processor 702 may be configured to generate signals for driving valves in the manifold 708 (or driving integrated circuits in communication with the valves) based on a comparison of the clock signal to a programmed pattern that indicates when the chambers of the pressure-mitigation device should be inflated or deflated.

In some embodiments, the processor 702 processes the pressure data prior to examination by the analysis module 706. For example, the processor 702 may apply algorithms designed for temporal aligning, artifact removal, and the like. In other embodiments, the analysis module 706 is designed to analyze the pressure data in its unprocessed (i.e., raw) form. As further discussed below, the processor 702 may forward at least some of the pressure data, in either its processed or unprocessed form, to the communication module 704 for transmittal to another computing device for analysis. By examining the pressure data in conjunction with flow data representative of the fluid flowing into the controller 700 from the pump(s), the analysis module 706 can control how the chambers of the pressure-mitigation device are inflated and/or deflated. For example, the analysis module 706 may be responsible for separately controlling the set point for fluid flowing into each chamber such that the pressures of the chambers match a predetermined pattern.

By examining the pressure data, the analysis module 706 may also be able to sense movements of the human body under which the pressure-mitigation device is positioned. These movements may be caused by the patient, another individual (e.g., a healthcare professional or an operator of the controller 700), or the underlying surface. The analysis module 706 may apply algorithm(s) to the data representative of these movements (also referred to as "movement data" or "motion data") to identify repetitive movements and/or random movements to better understand the health state of the patient. For example, the analysis module 706 may be able to produce a coverage metric indicative of the amount of time that the human body is properly positioned on the pressure-mitigation device. As further discussed below, the controller 700 (or another computing device) may be able to establish whether the pressure-mitigation device has been properly deployed/operated based on the coverage metric. As another example, the analysis module 706 may be able to establish the respiration rate, heart rate, or another vital measurement based on the movements of a patient. Generally, the movement data is derived from the pressure data. That is, the analysis module 706 may be able to infer movements of the human body by analyzing the pressure of the chambers of the pressure-mitigation device in conjunction with the rate at which fluid is being delivered to those chambers. Consequently, the pressure-mitigation device may not actually include any sensors for measuring movement, such as accelerometers, tilt sensors, or gyroscopes.

The analysis module 706 may respond in several ways after examining the pressure data. For example, the analysis module 706 may generate a notification (e.g., an alert) to be transmitted to another computing device by the communication module 704. The other computing device may be associated with a healthcare professional (e.g., a physician or a nurse), a family member of the patient, or some other entity (e.g., a researcher or an insurer). The communication module 704 may be, for example, wireless communication circuitry designed to establish communication channels with other computing devices. Examples of wireless communication circuitry include integrated circuits (also referred to as "chips") configured for Bluetooth, Wi-Fi, NFC, and the like. As another example, the analysis module 706 may cause the pressure data (or analyses of such data) to be integrated with the electronic health record of the patient. Generally, the electronic health record is maintained in a storage medium accessible to the communication module 704 across a network.

The controller 700 may include a power component 712 that is able to provide to the other components residing within the housing, as necessary. Examples of power components include rechargeable lithium-ion (Li-Ion) batteries, rechargeable nickel-metal hydride (NiMH) batteries, rechargeable nickel-cadmium (NiCad) batteries, etc. In some embodiments, the controller 700 does not include a power component, and thus must receive power from an external source. In such embodiments, a cable designed to facilitate the transmission of power (e.g., via a physical connection of electrical contacts) may be connected between the power interface 714 of the controller 700 and the external source. The external source may be, for example, an alternating current (AC) power socket or another electronic device.

Figure 8:
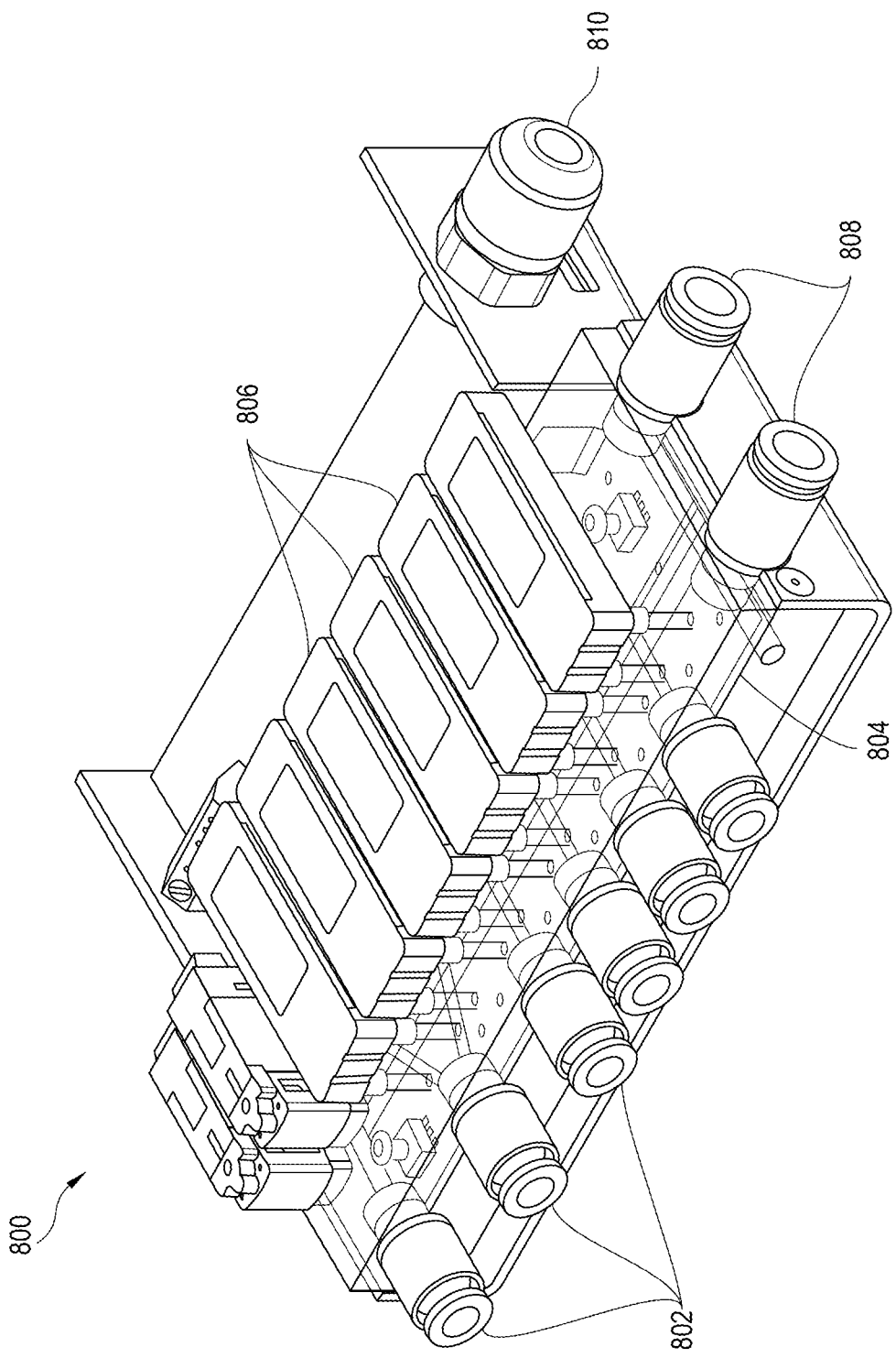
FIG. 8 is an isometric view of a manifold for controlling the flow of fluid (e.g., air) to the chambers of a pressure-mitigation device in accordance with embodiments of the present technology.

FIG. 8 is an isometric view of a manifold 800 for controlling the flow of fluid (e.g., air) to the chambers of a pressure-mitigation device in accordance with embodiments of the present technology. As discussed above, a controller can be configured to inflate and/or deflate the chambers of a pressure-mitigation device to create a pressure gradient that moves the main point of pressure applied by an object across the surface of a human body situated on the pressure-mitigation device. To accomplish this, the manifold 800 can guide fluid to the chambers through a series of valves 802. In some embodiments, each valve 802 corresponds to a separate chamber of the pressure-mitigation device. In some embodiments, at least one valve 802 corresponds to multiple chambers of the pressure-mitigation device. In some embodiments, at least one valve 802 is not used during operation. For example, if the pressure-mitigation device includes four chambers, multi-channel tubing may be connected between the pressure-mitigation device and four valves 802 of the manifold 800. In such embodiments, the other valves may remain sealed during operation.

Generally, the valves 802 are piezoelectric valves designed to switch from one state (e.g., an open state) to another state (e.g., a closed state) in response to an application of voltage. Each piezoelectric valve includes at least one piezoelectric element that acts as an electromechanical transducer. When a voltage is applied to the piezoelectric element, the piezoelectric element is deformed, thereby resulting in mechanical motion (e.g., the opening or closing of a valve). Examples of piezoelectric elements include disc transducers, bender actuators, and piezoelectric stacks.

Piezoelectric valves provide several benefits over other valves, such as linear valves and solenoid-based valves. First, piezoelectric valves do not require holding current to maintain a state. As such, piezoelectric valves generate almost no heat. Second, piezoelectric valves create almost no noise when switching between states, which can be particularly useful in medical settings. Third, piezoelectric valves can be opened and closed in a controlled manner that allows the manifold 800 to precisely approach a desired flow rate without overshoot or undershoot. In contrast, the other valves described above must be in either an open state, in which the valve is completely open, or a closed state, in which the valve is completely closed. Fourth, piezoelectric valves require very little power to operate, so a power component (e.g., power component 712 of FIG. 7) may only need to provide 3-6 watts to the manifold 800 at any given time. While embodiments of the manifold 800 may be described in the context of piezoelectric valves, other types of valves, such as linear valves or solenoid-based valves, could be used instead of, or in addition to, piezoelectric valves.

In some embodiments, the manifold 800 includes one or more transducers 806 and a circuit board 804 that includes one or more integrated circuits (also referred to as "chips") for managing communication with the valves 802 and the transducer(s) 806. Because these local chip(s) reside within the manifold 800 itself, the valves 802 can be digitally controlled in a precise manner. The local chip(s) may be connected to other components of the controller. For example, the local chip(s) may be connected to other components housed within the controller, such as processors (e.g., processor 702 of FIG. 7) and clock modules. The transducer(s) 806, meanwhile, can generate an electrical signal based on the pressure of each chamber of the pressure-mitigation device. Generally, each chamber is associated with a different valve 802 and a different transducer 806. Here, for example, the manifold includes six valves 802 capable of interfacing with the pressure-mitigation device, and each of these valves may be associated with a corresponding transducer 806. Pressure data representative of the values of the electrical signals generated by the transducer(s) 806 can be provided to other components of the controller for further analysis.

The manifold 800 may also include one or more compressors. In some embodiments each valve 802 of the manifold 800 is fluidically coupled to the same compressor, while in other embodiments each valve 802 of the manifold 800 is fluidically coupled to a different compressor. Each compressor can increase the pressure of fluid by reducing its volume before guiding the fluid to the pressure-mitigation device.

Fluid produced by a pump may initially be received by the manifold 800 through one or more ingress fluid interfaces 808 (or simply "ingress interfaces"). As noted above, in some embodiments, a compressor may then increase pressure of the fluid by reducing its volume. Thereafter, the manifold 800 can controllably guide the fluid into the chambers of a pressure-mitigation device through the valves 802. The flow of fluid into each chamber can be controlled by local chip(s) disposed on the circuit board 804. For example, the local chip(s) can dynamically vary the flow of fluid into each chamber in real time by controllably applying voltages to open/close the valves 802.

In some embodiments, the manifold includes one or more egress fluid interfaces 810 (or simply "egress interfaces"). The egress fluid interface(s) 810 may be designed for high pressure and high flow to permit rapid deflation of the pressure-mitigation device. For example, upon determining that an operator has provided input indicative of a request to deflate the pressure-mitigation device (or a portion thereof), the manifold 800 may allow fluid to travel back though the valve(s) 802 from the pressure-mitigation device and then out through the egress fluid interface(s) 810. Thus, the egress fluid interface(s) 810 may also be referred to as "exhausts" or "outlets." To provide the input, the operator may interact with a mechanical input component (e.g., mechanical input component 606 of FIG. 6A) or a digital input component (e.g., visible on display 610 of FIG. 6A).

Figure 9:
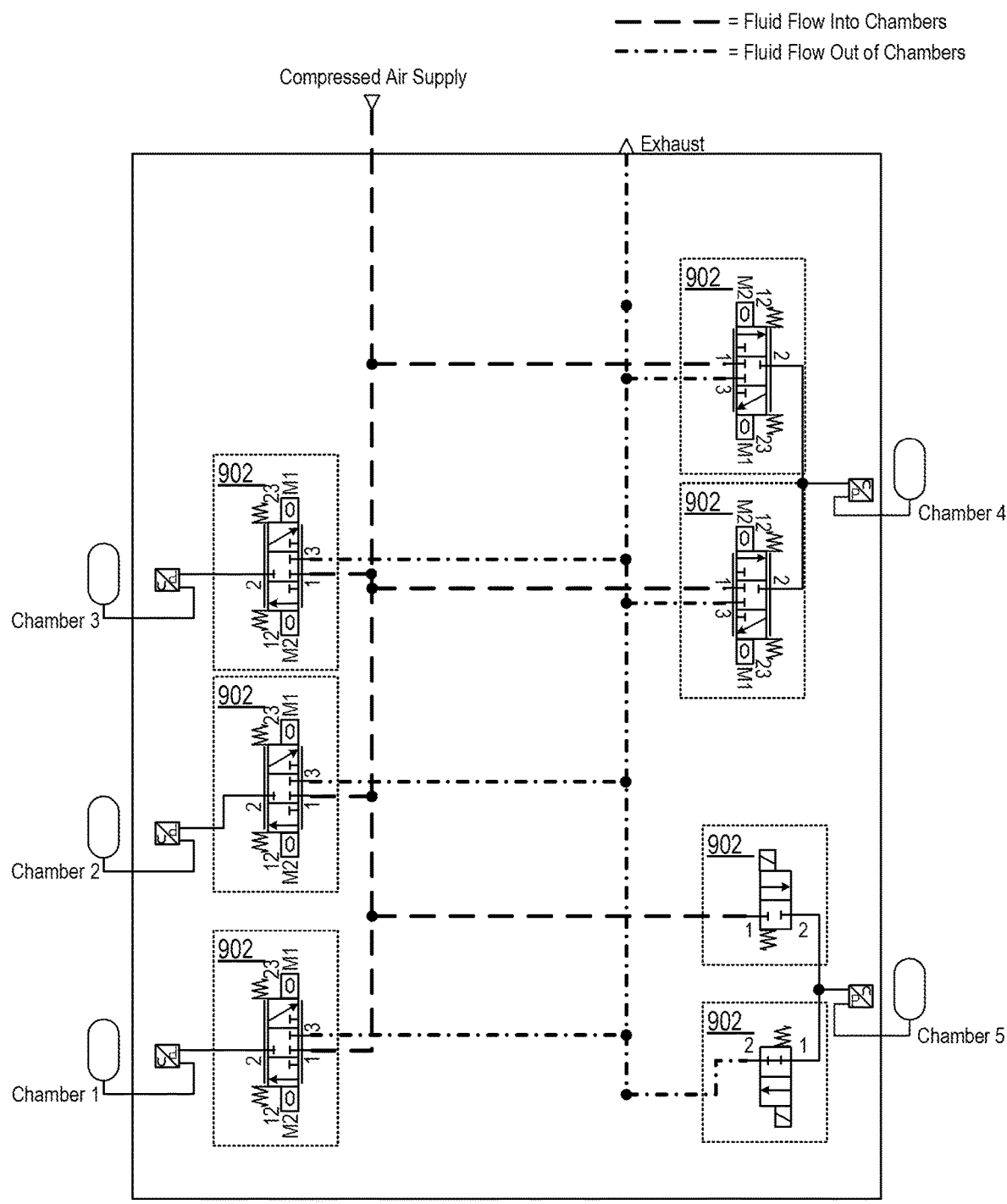
FIG. 9 is a generalized electrical diagram illustrating how the piezoelectric valves of a manifold can separately control the flow of fluid along multiple channels in accordance with embodiments of the present technology.

FIG. 9 is a generalized electrical diagram illustrating how the piezoelectric valves 902 of a manifold can separately control the flow of fluid along multiple channels in accordance with embodiments of the present technology. In FIG. 9, the manifold includes seven piezoelectric valves 902. Other embodiments of the manifold may include fewer than seven valves or more than seven valves. Fluid, such as air, can be guided by the manifold through the piezoelectric valves 902 to the chambers of a pressure-mitigation device. In FIG. 9, the manifold is fluidically connected to a pressure-mitigation device that has five chambers. However, in other embodiments, the manifold may be fluidically connected to a pressure-mitigation device that has fewer than five chambers or more than five chambers.

All of the piezoelectric valves 902 included in the manifold need not necessarily be identical to one another. Piezoelectric valves may be designed for high pressure and low flow, high pressure and high flow, low pressure and low flow, or low pressure and high flow. In some embodiments all of the piezoelectric valves included in the manifold are the same type, while in other embodiments the manifold includes multiple types of piezoelectric valves. For example, piezoelectric valves corresponding to side supports of the pressure-mitigation device may be designed for high pressure and high flow (e.g., to allow for a quick discharge of fluid stored therein), while piezoelectric valves corresponding to chambers of the pressure-mitigation device may be designed for high pressure and low flow. Moreover, some piezoelectric valves may support bidirectional fluid flow, while other piezoelectric valves may support unidirectional fluid flow. Generally, if the manifold includes unidirectional piezoelectric valves, each chamber in the pressure-mitigation device is associated with a pair of unidirectional piezoelectric valves to allow fluid flow in either direction. Here, for example, Chambers 1-3 are associated with a single bidirectional piezoelectric valve, Chamber 4 is associated with two bidirectional piezoelectric valves, and Chamber 5 is associated with two unidirectional piezoelectric valves.

The chambers of a pressure-mitigation device may be inflated/deflated for a predetermined duration of 15-180 seconds (e.g., 30 seconds, 60 seconds, 90 seconds, 120 seconds, 150 seconds, or any duration therebetween) in accordance with a predetermined pattern. Thus, the status of each chamber may be varied at least every 60 seconds, 90 seconds, 120 seconds, 240 seconds, etc. Generally, the predetermined pattern causes the chambers to be inflated/deflated in a non-identical manner. For example, if the pressure-mitigation device includes four chambers, the first and second chambers may be inflated for 30 seconds, the second and third chambers may be inflated for 45 seconds, the third and fourth chambers may be inflated for 30 seconds, and then the first and fourth chambers may be inflated for 45 seconds. These chambers may be inflated/deflated to a predetermined pressure level from 0-100 millimeters of mercury (mmHg) (e.g., 15 mmHg, 20 mmHg, 30 mmHg, 45 mmHg, 50 mmHg, or any pressure level therebetween). In some embodiments, the inflation pattern administered by the controller inflates/deflates two or more chambers at one time. In these embodiments, the chambers can be inflated/deflated to the same or different pressure levels, and the duration that the chambers are maintained at the pressure levels may be the same or different. For example, in the scenario above where the first and second chambers are inflated, the first chamber may be inflated to a pressure of 15 mm Hg while the second chamber may be inflated to a pressure of 30 mm Hg. In other embodiments, the controller can apply different inflation/deflation patterns to the individual chambers.

Methodologies for Managing Treatment Sessions

FIG. 10 is a flow diagram of a process 1000 for varying the pressure in the chambers of a pressure-mitigation device that is positioned between a human body and a surface in accordance with embodiments of the present technology. By varying the pressure in the chambers, a controller can move the main point of pressure applied by the surface across the human body. For example, the main point of pressure applied by the support surface to the human body may be moved amongst multiple predetermined locations by sequentially varying the pressure in different predetermined subsets of chambers. Note that the human body could be in nearly any position, with minimal changes to the process 1000. Thus, the pressure-mitigation device may be arranged so that pressure is relieved an anatomical region located along the anterior or posterior side of the human body.

Initially, a controller can determine that a pressure-mitigation device has been connected to the controller (step 1001). The controller may detect which type of pressure-mitigation device has been connected by monitoring the connection between a fluid interface (e.g., the fluid interface 608 of FIG. 6B) and the pressure-mitigation device. Each type of pressure-mitigation device may include a different type of connector. For example, a pressure-mitigation device designed for deployment on elongated objects (e.g., pressure-mitigation device 100 of FIGS. 1A-B) may include a first arrangement of magnets in its connector, and a pressure-mitigation device designed for deployment on non-elongated objects (e.g., the pressure-mitigation device of FIGS. 2A-B) may include a second arrangement of magnets in its connector. The controller may determine which type of pressure-mitigation device has been connected based on which magnets have been detected within a specified proximity. As another example, the pressure-mitigation device designed for deployment on elongated objects may include a beacon capable of emitting a first electronic signature, while the pressure-mitigation device designed for deployment on non-elongated objects may include a beacon capable of emitting a second electronic signature. Examples of beacons include Bluetooth beacons, USB beacons, and infrared beacons. A beacon may be configured to communicate with the controller via a wired communication channel or a wireless communication channel.

The controller can then identify a pattern that is associated with the pressure-mitigation device (step 1002). For example, the controller may examine a library of patterns corresponding to different pressure-mitigation devices to identify the appropriate pattern. The library of patterns may be stored in a local memory (e.g., the memory 710 of FIG. 7) or a remote memory accessible to the controller across a network. The controller may modify an existing pattern based on the pressure-mitigation device, the user, the ailment affecting the user, etc. For example, the controller may alter an existing pattern responsive to determining that the pattern includes instructions for more chambers than the pressure-mitigation device includes. As another example, the controller may alter an existing pattern responsive to determining that the weight of the user exceeds a predetermined threshold.

In some embodiments, the pattern is associated with a characteristic of the user in addition to, or instead of, the pressure-mitigation device. For example, the controller may examine a library of patterns corresponding to different ailments or different anatomical regions to identify the appropriate pattern. Thus, the library may include patterns associated with anatomical regions along the anterior side of the human body, patterns associated with anatomical regions along the posterior side of the human body, or patterns associated with different ailments (e.g., ulcers, strokes, etc.).

The controller can then cause the chambers of the pressure-mitigation device to be inflated in accordance with the pattern (step 1003). As discussed above, the controller can cause the pressure on one or more anatomical regions of the human body to be varied by controllably inflating one or more chambers, deflating one or more chambers, or any combination thereof.

One of the benefits of the system described herein is that the controller may be designed to produce data regarding the pressure of the chambers of the pressure-mitigation device. This pressure data can then be examined—by the controller or another computing device—in order to gain insights into the health of a person positioned on the pressure-mitigation device.

These insights can take various forms. As an example, a computer program may determine, based on the pressure data, that the person is no longer properly positioned on the pressure-mitigation device. This may occur if the pressure data indicates that the chamber(s) along one side of the pressure-mitigation device are experiencing more pressure than the chamber(s) along the other side of the pressure-mitigation device. As another example, a computer program may compute, based on the pressure data, the weight of the person positioned on the pressure-mitigation device. Generally speaking, the weight of the person may correspond to the pressure of the chambers given a known rate of fluid flow into those chambers. Over time, knowledge may be gained into how the weight of various individuals corresponds to the pressure of the chambers in the pressure-mitigation device. For example, pressure data associated with a set of individuals whose weights are known may be fed into a machine learning (ML) algorithm as training data by the computer program. The ML algorithm may derive, compute, or otherwise obtain a heuristic that indicates how the pressure of chambers in a pressure-mitigation device relates to the weight of the individual positioned thereon. This heuristic could then be used by the computer program to infer the weights of human bodies for which pressure data is available.

For the purpose of illustration, the processes of FIGS. 11 and 13-16 are described as being performed by a controller that is responsible for controlling inflation or deflation of a pressure-mitigation device. However, the steps of these processes could be performed by another computing device. Accordingly, the controller may simply transmit pressure data to another computing device in some embodiments, rather than analyze the pressure data itself. In such embodiments, a computer program executing on the computing device may be responsible for analyzing the pressure data. This computer program may be developed or supported by the same entity that owns or operates the pressure-mitigation device.

FIG. 11 is a flow diagram of a process 1100 for establishing movements of the human body situated on a pressure-mitigation device without placing any sensors in direct contact with the human body in accordance with embodiments of the present technology. Steps 1101-1103 of FIG. 11 may be at least generally similar to steps 1001-1003 of FIG. 10.

As mentioned above, the controller responsible for managing the inflation and/or deflation of the pressure-mitigation device may include one or more transducers that are configured to generate an electrical signal based on the pressure of each chamber of the pressure-mitigation device. For example, if the pressure-mitigation device includes three chambers into which fluid (e.g., air) can flow, the controller may include three transducers, each of which is operable to generate an electrical signal that is indicative of the pressure of a corresponding chamber. Accordingly, the controller may obtain pressure data that is representative of the values of the electrical signals generated by the transducer(s) (step 1104).

In some embodiments, one or more pressure sensors are located near, or embedded within, the surface of the pressure-mitigation device. For example, at least one pressure sensor may be collocated near each chamber of the pressure-mitigation device. These pressure sensors may be used in addition to, or instead of, the transducers to infer the pressure that is applied to various parts of the pressure-mitigation device by the human body positioned thereon. Normally, conductive piezo-resistive materials are used to produce the pressure sensors contained in the pressure-mitigation device. This means that the electrical resistance will change when a force is applied on the sensor (e.g., due to the human body applying pressure to the corresponding portion of the pressure-mitigation device). These pressure sensors can be used to detect motion of the human body. In particular, motions may be inferred based on changes in the pressure as detected by these pressure sensors. Motion data representative of the motions can be stored and/or shared (e.g., with other electronic devices) for further analysis. Data generated by the pressure sensors may be transmitted to the controller via a wired connection (e.g., via a data cable included in multi-channel tubing that is interconnected between the controller and pressure-mitigation device) or a wireless connection (e.g., via wireless communication circuitry included in the controller and pressure-mitigation device).

At a high level, the intrinsic motion of the human body may be measured by analyzing the motion data—either alone or in conjunction with pressure data and/or flow data. This motion data may be used as a barometer of health similar to other vital signs, such as blood pressure, heart rate, and oxygen saturation level, and thus may be used to predict well-being. In some embodiments, the motion data is used in a closed feedback loop to inform caregivers of the intrinsic motion (or lack thereof), which may be an indication of the health state and whether intervention is necessary. Assume, for example, that the motion data indicates that a patient consistently adjusts her position a small-yet-noticeable amount. If the motion data indicates that no such movements have occurred for an extended duration (e.g., 5×, 10×, or 20× the normal interval of time between movements), then the patient may have experienced a change in health that is worth noting to nearby caregivers. Note that the term "caregiver" may be used to refer to any person that provides care to a user of a pressure-mitigation device. Examples of caregivers include healthcare professionals, family members, friends, and the like.

Vital signs could also be inferred by the controller when establishing the health state, determining whether intervention is necessary, etc. For example, the controller may be able to infer the respiratory rate of the human body based on its motion as represented by the motion data. Examples of vital signs include blood pressure, heart rate, respiratory rate, oxygen saturation, and the like. The entire system, including the pressure-mitigation device and the controller, can be used in a feedback loop involving the patient and/or the caregiver as a means to communicate. The motion data may also indicate when the patient has left the pressure-mitigation device. Accordingly, the controller could be employed as part of a fall prevention system or fall detection system that generates notifications to alert caregivers of the patient's egress from the pressure-mitigation device. These notifications may be audible or non-audible. For instance, a notification (e.g., in the form of a text message, email message, or push notification) may be automatically delivered to a computing device associated with a caregiver responsive to a determination that the patient has left the pressure-mitigation device. Accordingly, the controller can be used to facilitate communication between the patient and her caregivers regarding her health state. For instance, the controller could be programmed to automatically contact emergency services (e.g., by dialing 911) in some situations, and the controller could be programmed to contact a primary healthcare provider in other situations.

The controller can then examine the pressure data to identify movements, if any, of the human body situated on the pressure-mitigation device (step 1105). Additionally or alternatively, the controller can examine the pressure data to identify a present location of the human body situated on the pressure-mitigation device. Accordingly, the controller may not only be able to monitor the location of the human body over time, but also detect changes in pressure that are indicative of movements. Such an approach allows for the mobility of the human body to be understood in a more holistic sense. By constantly monitoring the pressures of the chambers of the pressure-mitigation device, the controller may be able to infer the location of the human body without requiring the use of sensors that are in direct contact with the human body. Though, as noted above, pressure sensors could be incorporated into the pressure-mitigation device to provide greater insight into the location and movement of the human body.

As further discussed below, the controller may transmit at least some of the pressure data to a remote location for further analysis. For example, the controller may transmit the pressure data to a computing device for further analysis by a computer program executing thereon. As another example, the controller may transmit the pressure data to a network-accessible storage medium that could be subsequently accessed by a computer program executing on a computing device.

Unless contrary to physical possibility, it is envisioned that the steps described above may be performed in various sequences and combinations. For example, the controller may be configured to perform the processes 1000, 1100 of FIGS. 10 and 11 simultaneously. Other steps may also be included in some embodiments. As an example, the controller may cause a notification to be transmitted to another computing device in some situations. For instance, the controller may cause a notification to be transmitted to another computing device responsive to discovering a movement that is indicative of discomfort in an anatomical region of the human body situated on the pressure-mitigation device. One example of such a movement is shifting the pelvic region upward while in the supine position so as to relieve pressure on the sacral region. As another example, the controller may cause a notification to be transmitted to another computing device responsive to discovering a movement indicative of an attempt by the human body to leave the pressure-mitigation device or a complete lack of movement for a specified period of time.

Overview of Networked Pressure-Mitigation Systems

Remote monitoring of the pressure in the chambers of a pressure-mitigation device can be used to infer the health state of a person (also referred to as a "patient," "subject," or "user" of the pressure-mitigation device) situated thereon. For example, the pressure may be used to establish whether a user is presently mobile, or the pressure may be used to identify periods of complete immobility that may indicate a decline in the health state or a potential health complication. As further discussed below, remote monitoring may also detect when a user leaves the bed, chair, or other surface on which the patient-mitigation device is situated. In some embodiments, alerts are provided to draw attention to this movement. For example, the controller may generate a local alarm (e.g., an audible notification or visual notification) to draw attention to the movement. As another example, the controller may cause another computing device (e.g., a mobile phone) to generate a remote alarm to draw attention to the movement. Such an approach allows caregivers to assist when the user is ambulatory to avoid falls and/or identify falls from the surface in near real time without constant surveillance.

Remote monitoring can also be used to determine whether the user is properly using the pressure-mitigation device, whether the user is properly positioned on the pressure-mitigation device, or whether the user is using the pressure-mitigation device in compliance with a prescribed protocol. Based on this information, alerts can be generated by, or transmitted to, another computing device accessible by a healthcare facility (e.g., a hospital, clinic, or nursing home), a healthcare professional (e.g., a doctor, nurse, or therapist), or another individual who is responsible for providing care to the user. By analyzing the pressure data in real time, accurate alerts can be provided to caregivers, management (e.g., of the healthcare facility responsible for supplying the pressure-mitigation device), and others when the user is not compliant with the protocol and/or is improperly using the pressure-mitigation device (e.g., is positioned incorrectly), thereby promoting appropriate usage and enhancing the benefits of the system as a whole.

Figure 12:
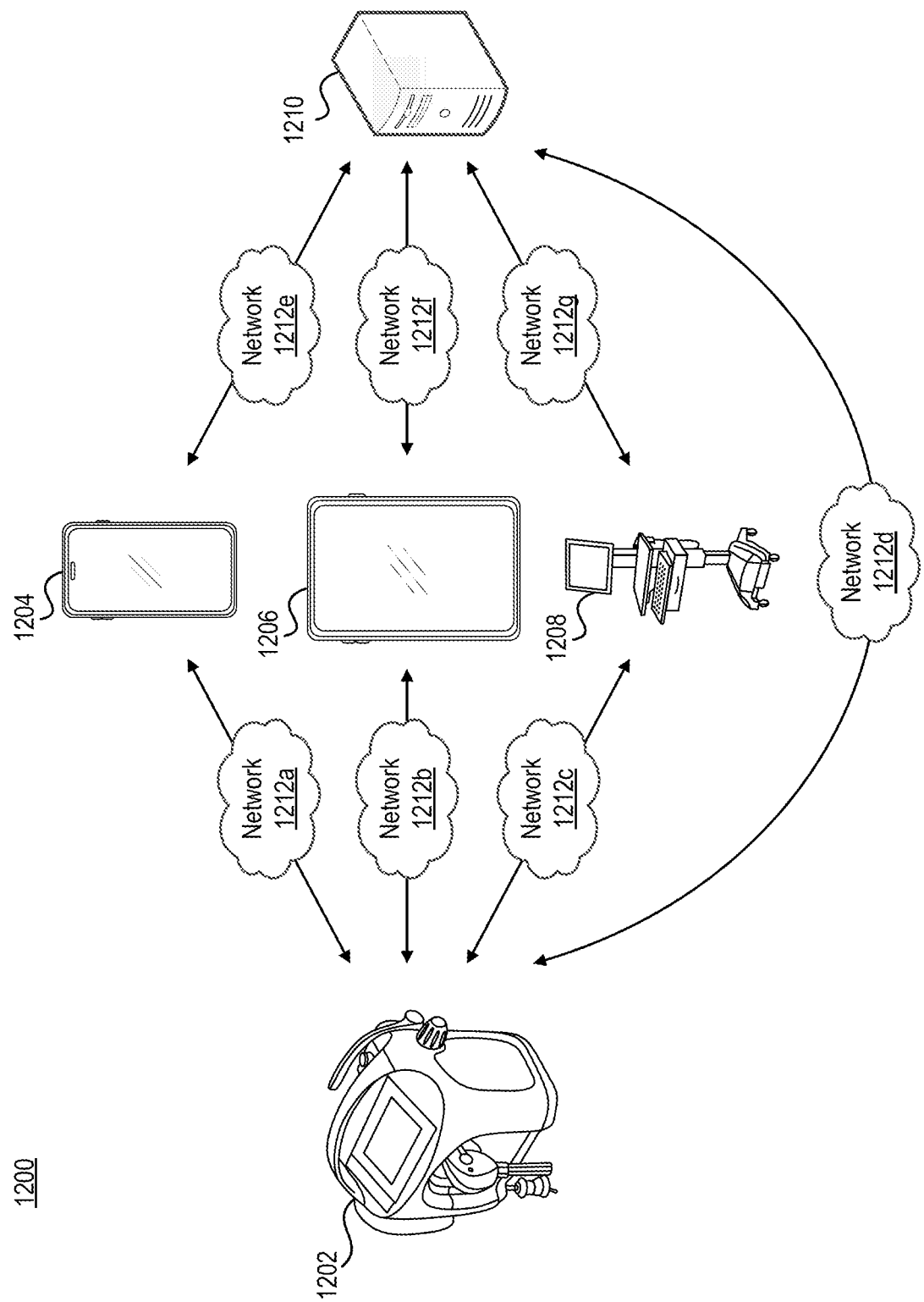
FIG. 12 depicts an example of a communication environment that includes a controller that is responsible for controlling inflation and/or deflation of a pressure-mitigation device (not shown).

FIG. 12 depicts an example of a communication environment 1200 that includes a controller 1202 that is responsible for controlling inflation and/or deflation of a pressure-mitigation device (not shown). As shown in FIG. 12, the controller 1202 can be configured to communicate with other computing devices. For example, the controller 1202 may transmit data to a given computing device, receive instructions from a given computing device, etc. Examples of computing devices include mobile phones 1204, tablet computers 1206, mobile workstations 1208, and computer servers 1210. The controller 1202 and computing devices may collectively be referred to as the "networked devices."

The networked devices can be connected to one another via one or more networks 1212*a-g*. The networks 1212*a-g* can include personal area networks (PANs), local area networks (LANs), wide area networks (WANs), metropolitan area networks (MANs), cellular networks, the Internet, etc. Additionally or alternatively, the networked devices may communicate with one another over a short-range communication protocol, such as Bluetooth, near-field communication (NFC), Wi-Fi, ZigBee, another commercial point-to-point protocol, or a proprietary point-to-point protocol. For example, the controller 1202 may include a Bluetooth Low Energy chipset, a Wi-Fi chipset, etc. In some embodiments, the controller 1202 is communicatively coupled to the mobile phone 1204 via a Bluetooth communication channel and the computer server 1210 via a Wi-Fi communication channel.

Embodiments of the communication environment may include some or all of the networked devices. For example, the communication environment 1200 may include the controller 1202 and a single computing device (e.g., the mobile phone 1204) that is responsible for examining data generated, derived, or otherwise obtained by the controller 1202.

As another example, the communication environment 1200 may include the controller 1202 and a computer server 1210 on which data is stored for subsequent review. In such embodiments, the computer server 1210 may examine data generated, derived, or otherwise obtained by the controller 1202, and the computer server 1210 may transmit analyses of the data to another computing device. For example, the computer server 1210 may transmit analyses of pressure data to the mobile phone 1204 for presentation to a caregiver.

FIG. 13 is a flow diagram of a process 1300 for establishing a value for a characteristic of the human body situated on a pressure-mitigation device based on an analysis of data representative of the pressure of the chambers of the pressure-mitigation device. Steps 1301-1304 may be at least generally similar to steps 1101-1104 of FIG. 11.

Here, however, the controller estimates a value for a characteristic of the human body based on the pressure data and/or information derived from the pressure data (step 1305). For example, the controller may be able to estimate the weight of the human body by examining the pressure data in conjunction with flow data representative of the fluid flowing into the controller (e.g., from one or more pumps). As another example, the controller may be able to estimate the respiration rate and/or the heart rate by examining movements of the human body inferred from the pressure data. Heartbeats may be associated with small changes in the pressure of at least one chamber of the pressure-mitigation device, while respirations (e.g., inhalations or exhalations) may be associated with slightly larger changes in the pressure of at least one chamber of the pressure-mitigation device. Generally, the pressure changes corresponding to heartbeats may only be detectable in a small subset of chambers (e.g., those located directly beneath the upper chest). Meanwhile, the pressure changes corresponding to respirations may be detectable in a larger subset of chambers. Accordingly, the controller may be able to understand aspects of the health of the human body, such as its state of mobility, in a noninvasive manner. As discussed above, pressure data could instead be filtered, processed, and examined to obtain information regarding motions related to blood pressure, heart rate, and respiratory rate.

In some embodiments, pressure data is examined by the controller in real time so as to continually establish the value of the characteristic of the human body. For example, the controller may estimate some characteristics (e.g., heart rate and respiratory rate) on an ongoing basis as constant insight into those characteristics may be critical to providing proper care. In other embodiments, pressure data is examined by the controller on an ad hoc basis so as to periodically establish the value of the characteristic of the human body. For example, the controller may estimate some characteristics (e.g., weight and blood pressure) on an infrequent basis as sporadic insight into those characteristics may be sufficient. Note that pressure data could be obtained in real time regardless of the frequency with which the pressure data is examined.

Thereafter, the controller may transmit information related to the characteristic to a destination across a network (step 1306). For example, the controller may transmit the information to a piece of healthcare equipment that is accessible to a caregiver responsible for managing the human body situated on the pressure-mitigation device. Examples of healthcare equipment include mobile workstations, ventilators, pulse oximeters, monitors, and other computing devices situated in healthcare facilities. As another example, the controller may transmit the information to a computing device that is associated with the caregiver. Examples of computing devices include mobile phones, tablet computers, and wearable electronic devices such as watches and fitness trackers. As another example, the controller may transmit the information to a computer server on which information regarding deployed pressure-mitigation devices is stored. The information may not only include the value for the characteristic, but also details regarding how the value was estimated. For example, the information may include the subset of pressure data that was used to estimate the value, operating conditions of the controller (e.g., rate of fluid flow into the chambers of the pressure-mitigation device), and the like.

As further discussed with reference to FIG. 16, the controller may also be able to detect instances of medical events based on patterns of values discovered in the motion data that are indicative of certain motions. These patterns of values may be discovered by applying computer-implemented models (or simply "models") that are trained to detect patterns that may be representative of medical events to the pressure data. One example of a medical event is a seizure. During a seizure, the human body will experience violent muscle contractions that correspond to high-frequency spikes in pressure within the chambers of the pressure-mitigation device. Accordingly, if a series of high-frequency spikes are discovered over a short interval of time (e.g., 3 seconds, 5 seconds, or 10 seconds), then the controller may infer that the patient placed thereon has experienced a seizure and then take appropriate action (e.g., notify a caregiver).

Such analysis of the pressure data could additionally or alternatively be performed by another computing device, such as a mobile phone, tablet computer, mobile workstation, or computer server. For example, "light" analysis may be performed by the controller using less resource-intensive heuristics, algorithms, or models, while "heavy" analysis may be performed by the other computing device using more resource-intensive heuristics, algorithms, or models.

In embodiments where another computing device analyzes the pressure data, the controller may transmit the pressure data (or information derived from the pressure data) to the other computing device. For example, the pressure data may be transmitted to a computer server that is communicatively connected to the controller. The computer server may be directly connected to the controller, or the computer server may be indirectly connected to the controller via one or more intermediary computing devices. The computer server can examine the pressure data and then produce an output that is indicative of an estimated value for a characteristic of the human body. For example, the computer server may apply an algorithm to identify one or more values that define a variation in the pressure data that matches a pattern in accordance with a pattern-defining parameter. The computer server can then generate a notification that specifies the output. The notification may be transmitted to the controller or another computing device. For example, the computer server may transmit the notification to a mobile phone associated with a caregiver responsible for providing care to a user of a pressure-mitigation device or an administrator of the healthcare facility in which the user is located. As another example, the computer server may transmit the notification to a mobile workstation that is located in proximity to the controller (and thus the pressure-mitigation device and user). The notification may be delivered in the form of a push notification, email message, Short Message Service (SMS) message (also referred to as a "text message"), etc.

The controller may be deployed as part of a closed loop system that is designed to autonomously infer information related to the health of a user of a pressure-mitigation device based on an analysis of data indicative of the pressure of the chambers of the pressure-mitigation device. Thus, the controller (or some other computing device) may be configured to examine the pressure data to determine whether the pressure-mitigation device has been properly deployed, whether adjustments of the user are needed, etc. For example, the pressure data may be examined to determine whether the values indicate that the user has been properly situated on the pressure-mitigation device. In the event that the pressure data indicates that the user is not properly situated on the pressure-mitigation device, a notification may be generated (e.g., by the controller) so that corrective action can be taken, thereby ensuring that the pressure-mitigation device is able to provide therapy as intended.

FIG. 14 is a flow diagram of a process 1400 for producing a coverage metric that indicates whether a pressure-mitigation device is being operated in accordance with a treatment regimen (also referred to as a "treatment program"). The controller may execute the process 1400 on a periodic or continual basis so that real-time feedback can be provided regarding whether the pressure-mitigation device is being deployed properly. While the process 1400 is described as being performed by a controller, those skilled in the art will recognize that the process 1400 could be partially or entirely performed by another computing device, such as a mobile phone, tablet computer, mobile workstation, or computer server.

Initially, the controller obtains data indicative of the pressure of the chambers of a pressure-mitigation device that is presently deployed (step 1401). The controller can then examine the pressure data to infer a location, position, or orientation of the human body situated on the pressure-mitigation device (step 1402). The location, position, or orientation may be inferred based on an analysis of the pressure data in conjunction with data representative of fluid flowing into the pressure-mitigation device. Normally, the fluid flows through the controller as discussed above with reference to FIGS. 6A-9. However, the fluid could flow directly from a source (e.g., one or more pumps) into the pressure-mitigation device in embodiments where the controller manages the rate at which the fluid flows into the chambers of the pressure-mitigation device through control of the source. As an example, the controller may infer that the human body is located above a given chamber responsive to discovering that its pressure in higher than expected based on the amount of fluid being directed into the given chamber. Analysis of the feedback (e.g., as indicated in the pressure data generated for the human body) can be performed to ascertain the location of the human body in relation to the pressure-mitigation device. More specifically, the location of the human body may be established by monitoring the pressure of individual cells of the pressure-mitigation device. This information could be used, for example, to generate an alert that indicates the human body is improperly positioned over the pressure-mitigation device, which may prompt a caregiver to reposition the human body. In short, the controller may confirm that the pressure-mitigation device is being used properly to ensure the greatest efficacy for the human body. By monitoring the observed pressure versus the expected pressure on a per-cell basis, the location of the human body in relation to the pressure-mitigation device can also be established and then tracked over time. This may be helpful if, for example, the human body has little motor control or moves unexpectedly (e.g., due to spasms). Moreover, the controller may be able to infer movements of the human body by analyzing the pressure data. These movements may be caused by the user, another individual (e.g., a caregiver or an operator of the controller), or the underlying surface on which the pressure-mitigation device is deployed.

Then, the controller can produce data (also referred to as "movement data" or "motion data") that is representative of the location, position, or orientation of the human body (step 1403). The controller may calculate a coverage metric indicative of the amount of time that the human body has been properly positioned on the pressure-mitigation device based on the pressure data, motion data, or any combination thereof (step 1404). That is, the controller may analyze pressure data and/or motion data to calculate the amount of proper usage of the pressure-mitigation device (and thus infer the proper amount of therapy to be delivered by the pressure-mitigation device) over any given interval of time. This metric can be used as a quality and performance improvement measure, whereby feedback can be provided to caregivers regarding how the pressure-mitigation device was employed—either properly or improperly—in various scenarios. Real-time feedback could also be given to caregivers to allow for proper positioning of the human body over the pressure-mitigation device in order to ensure optimal therapy delivery.

In some embodiments, the coverage metric is calculated based on a subset of the pressure data and/or the motion data. For example, the controller could calculate the coverage metric using pressure data and/or motion data corresponding to a predetermined interval of time (e.g., 2 hours, 4 hours, 8 hours, 12 hours, or 24 hours). As another example, the controller could calculate the coverage metric using pressure data and/or motion data that follows receipt of input indicative of an acknowledgement that the user has been situated on the pressure-mitigation device. To provide the input, an operator may interact with a mechanical input component (e.g., mechanical input component 606 of FIG. 6A) or a digital input component (e.g., visible on display 610 of FIG. 6A) accessible on the controller. Alternatively, the operator may indicate that the user has been situated on the pressure-mitigation device through an interface generated by a computer program executing on a computing device, such as a mobile phone, tablet computer, or mobile workstation.

The controller may cause presentation of a notification that specifies the coverage metric or a recommendation based on the coverage metric (step 1405). The notification may be presented to indicate whether the user is properly arranged over the pressure-mitigation device. For example, a notification may be presented to a caregiver responsive to determining that the user is not properly arranged over the pressure-mitigation device (and thus must be moved). As another example, a notification may be presented to an administrator associated with a hospital responsive to determining that the coverage metric falls beneath a predetermined threshold (e.g., 75%, 80%, 90%, or 95% of a given interval of time). Accordingly, notifications may be generated on an ad hoc basis based on whether certain conditions are met.

FIG. 15 is a flow diagram of a process 1500 for establishing whether a pressure-mitigation device that is deployed beneath a human body is being used in compliance with a treatment regimen. Generally speaking, the treatment regimen may require that the human body be situated in a particular position with respect to the chambers of the pressure-mitigation device. For example, to ensure pressure applied by an underlying surface to an anatomical region of the human body is relieved, the anatomical region may need to be centrally located over the center of the geometric pattern of chambers.

Initially, a controller may cause the chambers of the pressure-mitigation device to be inflated or deflated to varying degrees in accordance with a programmed pattern (step 1501). Step 1501 of FIG. 15 may be at least generally similar to step 1003 of FIG. 10 and step 1103 of FIG. 11. Accordingly, the controller may control the flow of fluid (e.g., air) into each chamber so as to inflate and/or deflate chambers in a controlled manner to lessen the pressure applied to the human body by the surface of the object on which the pressure-mitigation device is deployed.

Thereafter, the controller can obtain data that indicates the pressure of at least some of the chambers of the pressure-mitigation device (step 1502). Normally, this pressure data indicates the pressure of each chamber of the pressure-mitigation device, though the pressure data may only indicate the pressure of some chambers of the pressure-mitigation device in some embodiments. This pressure data may be based on electrical signals generated by transducers mounted in the controller, or this pressure data may be based on pressure sensors embedded in the pressure-mitigation device. The controller can then examine this pressure data so as to establish a location of the human body with respect to the chambers (step 1503). Normally, the chambers of the pressure-mitigation device are arranged in a geometric pattern that is designed to alleviate pressure on an anatomical region as discussed above. By examining the pressure of individual chambers, the controller may be able to infer the location of the human body with respect to the geometric pattern. For example, if chambers along opposing sides of the pressure-mitigation device have roughly equal pressures, the controller may infer that the human body is centered over the geometric pattern. Conversely, if the controller discovers that the chambers along one side of the pressure-mitigation device have higher pressures, then the controller may infer that the human body is likely positioned closer to that side of the pressure-mitigation device.

The controller can then produce, based on the location, an output that indicates whether the human body is properly positioned on the pressure-mitigation device as required by the treatment regimen (step 1504). For example, the controller may generate an audible notification or visual notification responsive to a determination that the human body is not properly positioned on the pressure-mitigation apparatus. As another example, the controller may transmit a notification to a computing device associated with a caregiver that specifies the human body is not properly positioned on the pressure-mitigation apparatus. Accordingly, the controller may be able to generate appropriate notifications to ensure that the pressure-mitigation device is being used as intended to ensure the greatest efficacy for the human body.

In some embodiments, the controller transmits information related to the output to a destination across a network (step 1505). For example, if the human body is representative of a patient of a healthcare facility, the controller may transmit the information to a computer server that includes data regarding patients of the healthcare facility. Additionally or alternatively, the controller may transmit the information to a computer server that is managed by a healthcare service that owns or operates pressure-mitigation devices. As another example, the controller may transmit the information to a computing device that is associated with the caregiver. The information may not only include the output itself, but also details regarding how the output was produced. For example, the information may include the subset of pressure data that was used to produce the output, operating conditions of the controller (e.g., rate of fluid flow into the chambers of the pressure-mitigation device), and the like.

The controller may perform these steps repeatedly in order to gain a better understanding of whether the pressure-mitigation device is being used as intended. For example, the controller may continually perform steps 1502-1504 over an interval of time as pressure data becomes available in order to produce a coverage metric that is indicative of the portion of the interval of time that the human body was properly positioned on the pressure-mitigation device. The coverage metric may provide insights into usage of the pressure-mitigation device that might not otherwise be available. Assume, for example, that the human body spends several days situated on the pressure-mitigation device without much improvement in the health state. In such a scenario, the coverage metric may be helpful in understanding why there has been minimal improvement. As an example, if the coverage metric indicates that the human body spends little time (e.g., less than 70 percent or 50 percent) in the proper position, then the lack of improvement may be largely, if not entirely, explainable by improper usage of the pressure-mitigation device.

FIG. 16 is a flow diagram of a process 1600 for discovering occurrences of medical events through analysis of data related to the pressure of chambers of a pressure-mitigation device. At a high level, occurrences of medical events may be inferred through the discovery of patterns of values that are indicative of movements corresponding to those medical events. As an example, a controller may be able to detect seizures by identifying high-frequency spikes in pressure of the chambers of a pressure-mitigation device that correspond to the violent muscle contractions that accompany a seizure.

Initially, a controller may obtain data that indicates the pressure of each of multiple chambers of a pressure-mitigation device over an interval of time (step 1601). Step 1601 of FIG. 16 may be at least generally similar to step 1401 of FIG. 14 and step 1502 of FIG. 15. Then, the controller parse the pressure data to discover a pattern of values that is indicative of a medical event experienced by the human body situated on the pressure-mitigation device (step 1602). For example, the controller may identify a heuristic, algorithm, or model that corresponds to the medical event, and then the controller may apply the heuristic, algorithm, or model to the pressure data in order to identify the pattern of values. In embodiments where the controller applies an algorithm or model, the algorithm or model may be trained using multiple series of values corresponding to confirmed instances of the medical event experienced by other individuals. Thus, the algorithm or model may be trained to identify instances of the medical event by learning from past instances of the medical event experienced by other individuals. The heuristic, meanwhile, may simply be programmed to identify values that match a pattern. For example, the heuristic may be programmed to identify intervals of time where multiple high-frequency spikes occur in short succession (e.g., over the course of 3 seconds, 5 seconds, or 10 seconds).

The controller can then generate a notification responsive to a determination that the medical event occurred based on the discovery of the pattern of values (step 1603). For example, the controller may generate an audible notification or visual notification that is noticeable by nearby individuals. As another example, the controller may cause transmission of the notification to a computing device that is associated with a caregiver responsible for managing the human body. At a high level, the notification may serve as a prompt for further action—either by the person situated on the pressure-mitigation device or another individual. Accordingly, it may be particularly beneficial to perform the steps of the process 1600 in real time so that medical events can be attended to appropriately.

Overview of Pressure-Mitigation Systems

Figure 17:
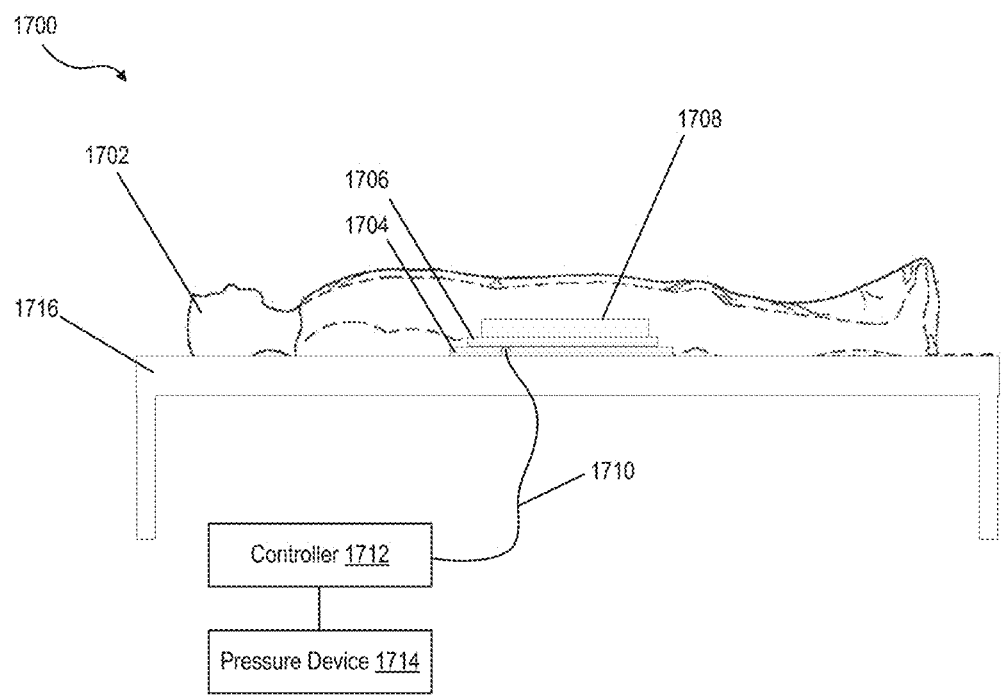
FIG. 17 is a partially schematic side view of a pressure-mitigation system (or simply "system") for orienting a user over a pressure-mitigation device in accordance with embodiments of the present technology.

FIG. 17 is a partially schematic side view of a pressure-mitigation system 1700 (or simply "system") for orienting a patient 1702 (also referred to as a "user" or "subject") over a pressure-mitigation device 1706 in accordance with embodiments of the present technology. Here, the system 1700 includes a pressure-mitigation device 1706 that include side supports 1708, an attachment device 1704, a pressure device 1714, and a controller 1712. Other embodiments of the system 1700 may include a subset of these components. For example, the system 1700 may include a pressure-mitigation device 1706, a pressure device 1714, and a controller 1712. The pressure-mitigation device 1706 is discussed in further detail with respect to FIGS. 1A-3, and the controller 1712 is discussed in further detail with respect to FIGS. 6A-9.

Figure 18A:
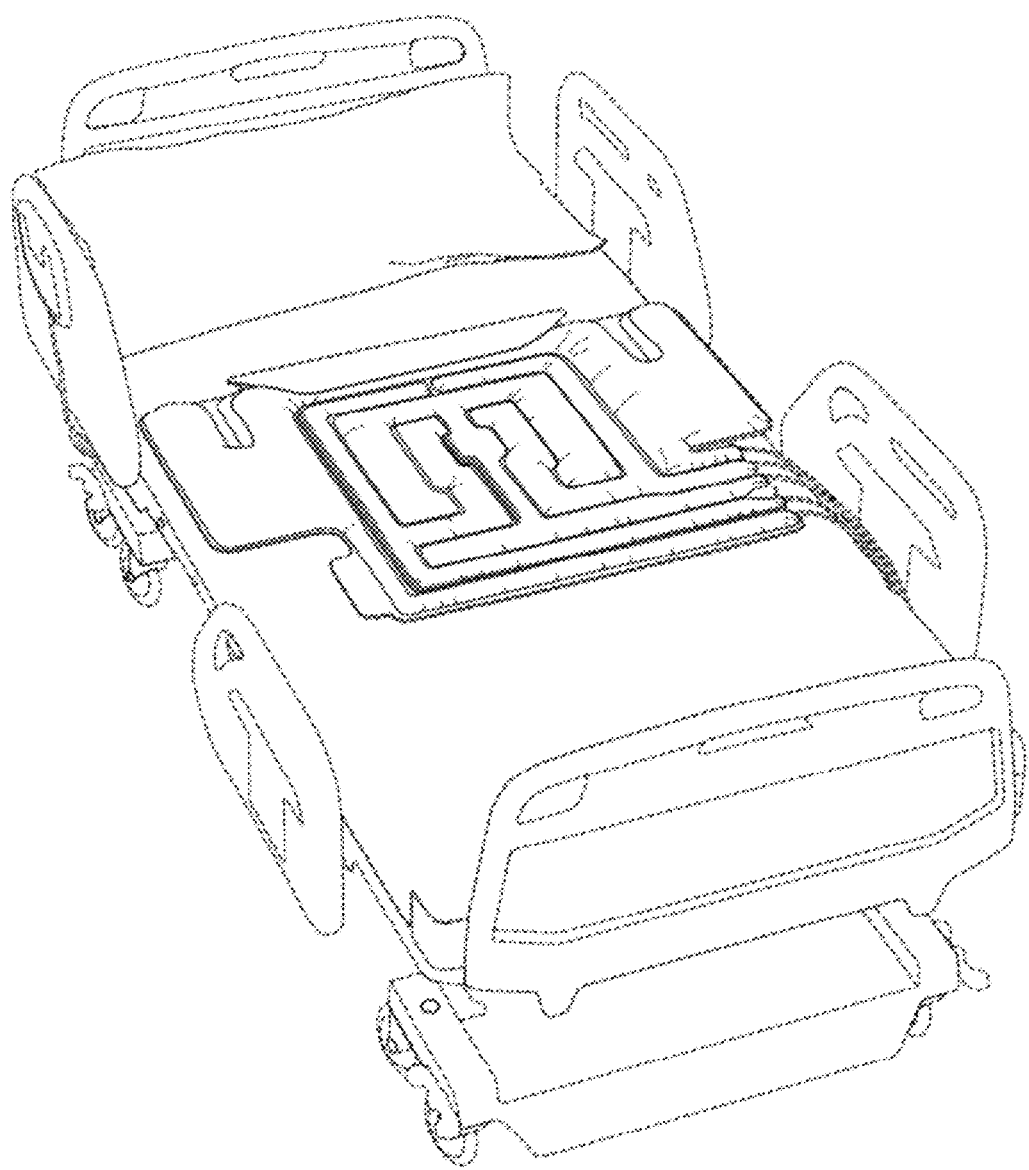
FIG. 18A illustrates an example of a pressure-mitigation device that includes a pair of elevated side supports that has been deployed on the surface of an object (here, a hospital bed).
Figure 18B:
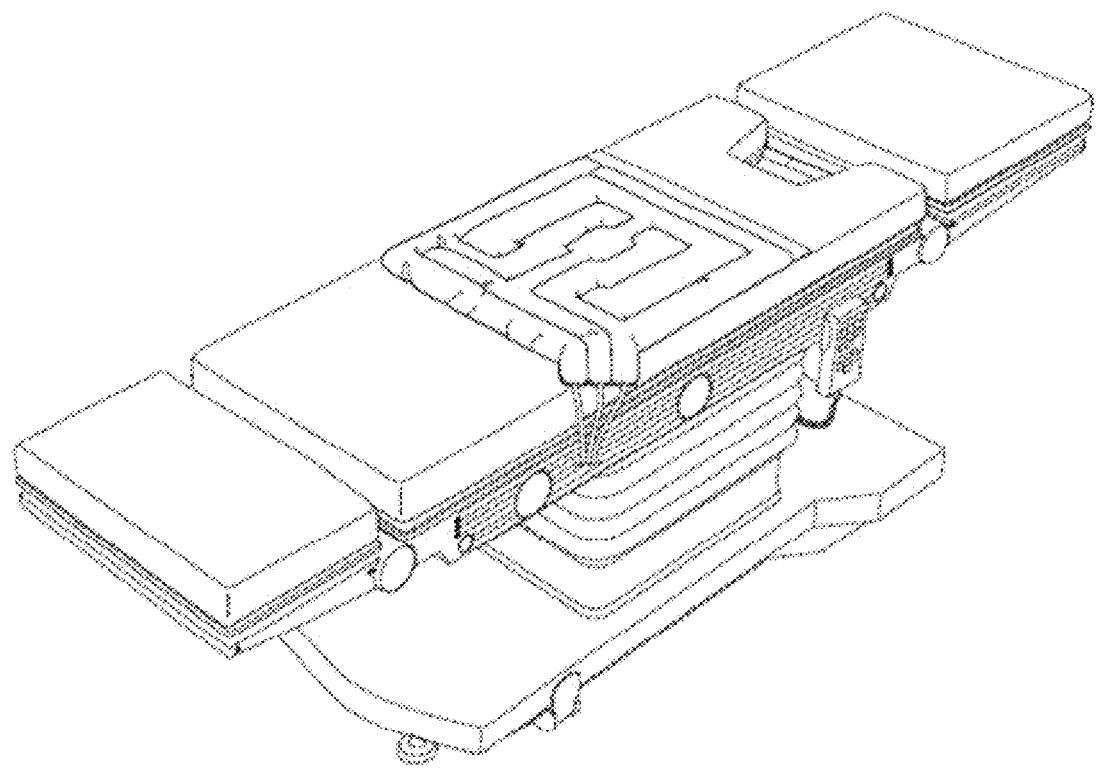
FIG. 18B illustrates an example of a pressure-mitigation device with no elevated side supports that has deployed on the surface of an object (here, an operating table).

In this embodiment, the pressure-mitigation device 1706 includes a pair of elevated side supports 1708 that extend longitudinally along opposing sides of the pressure-mitigation device 1706. FIG. 18A illustrates an example of a pressure-mitigation device that includes a pair of elevated side supports that has been deployed on the surface of an object (here, a hospital bed). However, some embodiments of the pressure-mitigation device 1706 do not include any elevated side supports. For example, side supports may not be necessary if the object on which the user 1702 is positioned includes lateral structures that prevent or inhibit horizontal movement, or if the user 1702 will be completely immobilized (e.g., using anesthesia). FIG. 18B illustrates an example of a pressure-mitigation device with no elevated side supports that has deployed on the surface of an object (here, an operating table). The pressure-mitigation device 1706 includes a series of chambers that may be arranged in a geometric pattern designed to mitigate the pressure applied to an anatomical region by the surface of the object 1716.

The elevated side supports 1708 can be configured to actively orient the anatomical region of the user 1702 over the series of chambers. For example, the elevated side supports 1708 may be responsible for actively orienting the anatomical region widthwise over the center of the geometric pattern. As shown in FIG. 17, the anatomical region may be the sacral region. However, the anatomical region could be any region of the human body that is susceptible to pressure. The elevated side supports 1708 may be configured to be ergonomically comfortable. For example, if the user 1702 is to be situated in the supine position, the elevated side supports 1708 may include a recess designed to accommodate the forearm that permits pressure to be offloaded from the elbow. The elevated side supports 1708 may be significantly larger in size than the chambers of the pressure-mitigation device 1706. Accordingly, the elevated side supports 1708 may create a barrier that restricts lateral movement of the user 1702. In some embodiments, the elevated side supports are approximately 2-3 inches taller in height as compared to the average height of an inflated chamber. Because the elevated side supports 1706 straddle the user 1702, the elevated side supports 1708 can act as barriers for maintaining the position of the user 1702 on top of the pressure-mitigation device 1706. As discussed above, the elevated side supports 1708 may be omitted in some embodiments. For example, the elevated side supports 1708 may be omitted if the user 1702 suffers from impaired mobility due to physical injury anesthesia, or some other condition that limits natural movement. As another example, the elevated side supports 1708 may be omitted if the object 1716 upon which the user 1702 and pressure-mitigation device 1706 are situated has structural components that limit movement.

In some embodiments, the inner side walls of the elevated side supports 1708 form, following inflation, a firm surface at a steep angle of orientation with respect to the pressure-mitigation device 1706. For example, the inner side walls may be on a plane of approximately 115 degrees, plus or minus 24 degrees, from the plane of the pressure-mitigation device 1706. These steep inner side walls can form a channel that naturally positions the user 1702 over the chambers of the pressure-mitigation device 1706. Thus, inflation of the elevated side supports 1708 may actively force the user 1702 into the appropriate position for mitigating pressure by orienting the body in the correct location with respect to the chambers of the pressure-mitigation device 1706.

After the initial inflation cycle has been completed, the pressure of each elevated side support 1708 may be lessened to increase comfort and prevent excessive force against the lateral sides of the user 1702. Oftentimes, a healthcare professional will be present during the initial inflation cycle to ensure that the elevated side supports 1708 properly position the user 1702 over the pressure-mitigation device 1706.

The controller 1712 can be configured to regulate the pressure of each chamber in the pressure-mitigation device 1706 (and the elevated side supports 1708, if included) via one or more flows of fluid generated by a pressure device 1714. One example of a pressure device is an air pump. These flow(s) of fluid can be guided from the controller 1712 to the pressure-mitigation device 1706 via multi-channel tubing 1710. For example, the chambers may be controlled in a specific pattern to reduce the pressure applied to the user 1702 by the surface of the underlying object 1716 when inflated (i.e., pressurized) and deflated (i.e., depressurized) in a coordinated fashion by the controller 1712, thereby preserving blood flow to the anatomical region positioned adjacent to the pressure-mitigation device 1706. As shown in FIG. 17, the multi-channel tubing 1710 may be connected between the pressure-mitigation device 1706 and the controller 1712. Accordingly, the pressure-mitigation device 1706 may be fluidically coupled to a first end of tubing (e.g., single-channel tubing or multi-channel tubing) while the controller 1712 may be fluidically coupled to a second end of the tubing. While the pressure device 1714 is normally housed within the controller 1712, these components could also be connected via multi-channel tubing. Thus, the pressure device 1714 may be fluidically coupled to a first end of tubing (e.g., single-channel tubing or multi-channel tubing) while the controller 1712 may be fluidically coupled to a second end of tubing.

Processing System

Figure 19:
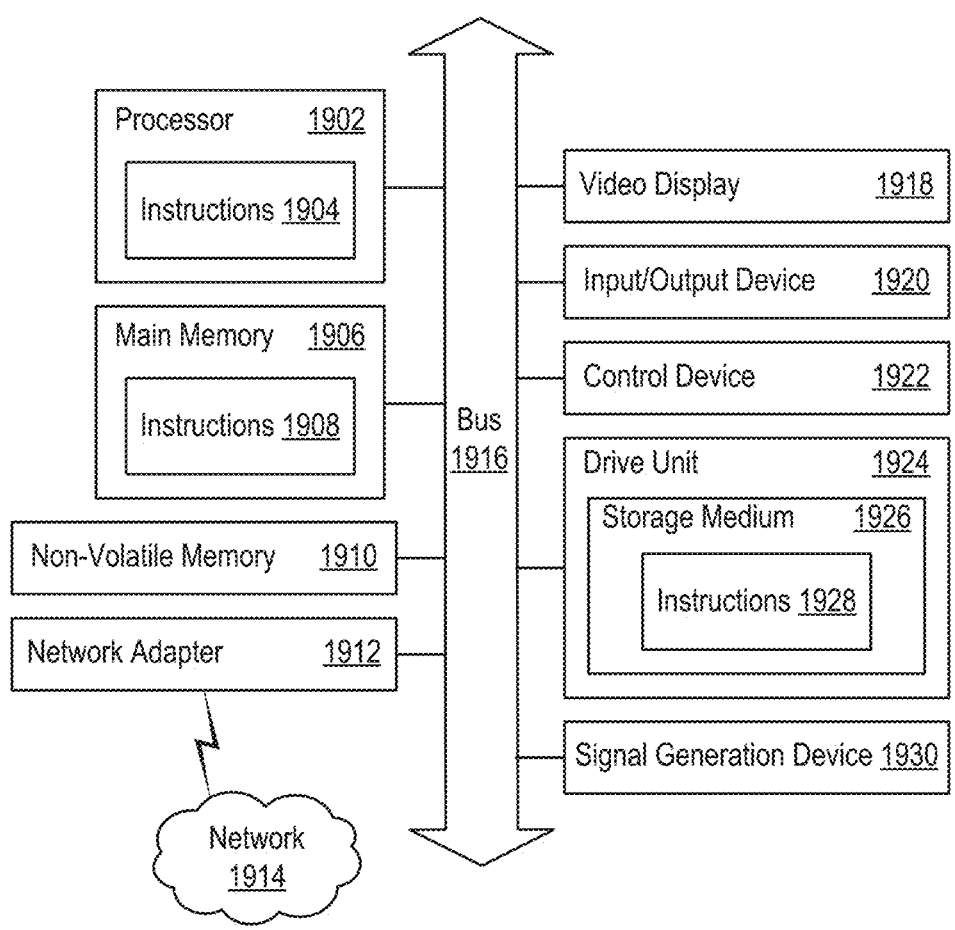
FIG. 19 is a block diagram illustrating a processing system in which at least some operations described herein can be implemented.

FIG. 19 is a block diagram illustrating an example of a processing system 1900 in which at least some operations described herein can be implemented. For example, components of the processing system 1900 may be hosted on a controller (e.g., controller 1712 of FIG. 17) responsible for controlling the flow of fluid to a pressure-mitigation device (e.g., pressure-mitigation apparatus 1706 of FIG. 17). As another example, components of the processing system 1900 may be hosted on a computing device that is communicatively coupled to the controller.

The processing system 1900 may include a processor 1902, main memory 1906, non-volatile memory 1910, network adapter 1912 (e.g., a network interface), video display 1918, input/output device 1920, control device 1922 (e.g., a keyboard, pointing device, or mechanical input such as a button), drive unit 1924 that includes a storage medium 1926, or signal generation device 1930 that are communicatively connected to a bus 1916. The bus 1916 is illustrated as an abstraction that represents one or more physical buses and/or point-to-point connections that are connected by appropriate bridges, adapters, or controllers. The bus 1916, therefore, can include a system bus, Peripheral Component Interconnect (PCI) bus, PCI-Express bus, HyperTransport bus, Industry Standard Architecture (ISA) bus, Small Computer System Interface (SCSI) bus, Universal Serial Bus (USB), Inter-Integrated Circuit ($I^2C$) bus, or bus compliant with Institute of Electrical and Electronics Engineers (IEEE) Standard 1394.

The processing system 1900 may share a similar computer processor architecture as that of a computer server, router, desktop computer, tablet computer, mobile phone, video game console, wearable electronic device (e.g., a watch or fitness tracker), network-connected ("smart") device (e.g., a television or home assistant device), augmented or virtual reality system (e.g., a head-mounted display), or another electronic device capable of executing a set of instructions (sequential or otherwise) that specify action(s) to be taken by the processing system 1900.

While the main memory 1906, non-volatile memory 1910, and storage medium 1924 are shown to be a single medium, the terms "storage medium" and "machine-readable medium" should be taken to include a single medium or multiple media that stores one or more sets of instructions 1926. The terms "storage medium" and "machine-readable medium" should also be taken to include any medium that is capable of storing, encoding, or carrying a set of instructions for execution by the processing system 1900.

In general, the routines executed to implement the embodiments of the present disclosure may be implemented as part of an operating system or a specific application, component, program, object, module, or sequence of instructions (collectively referred to as "computer programs"). The computer programs typically comprise one or more instructions (e.g., instructions 1904, 1908, 1928) set at various times in various memories and storage devices in a computing device. When read and executed by the processor 1902, the instructions cause the processing system 1900 to perform operations to execute various aspects of the present disclosure.

While embodiments have been described in the context of fully functioning computing devices, those skilled in the art will appreciate that the various embodiments are capable of being distributed as a program product in a variety of forms. The present disclosure applies regardless of the particular type of machine- or computer-readable medium used to actually cause the distribution. Further examples of machine- and computer-readable media include recordable-type media such as volatile memory and non-volatile memory 1910, removable disks, hard disk drives, optical disks (e.g., compact disc read-only memory (CD-ROMs) and Digital Versatile Discs (DVDs)), cloud-based storage, and transmission-type media such as digital and analog communication links.

The network adapter 1912 enables the processing system 1900 to mediate data in a network 1914 with an entity that is external to the processing system 1900 through any communication protocol supported by the processing system 1900 and the external entity. The network adapter 1912 can include a network adaptor card, a wireless network interface card, a switch, a protocol converter, a gateway, a bridge, a hub, a receiver, a repeater, or a transceiver that includes an integrated circuit (e.g., enabling communication over Bluetooth or Wi-Fi).

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

I claim:
1. A controller comprising:
a structural body that includes
an ingress interface to which tubing is connectable, the tubing allowing the ingress interface to be fluidically coupled to a pump that is external to the controller, and
an egress interface to which multi-channel tubing is connectable, the multi-channel tubing allowing the egress interface to be fluidically coupled to a pressure-mitigation device that is disposed between a human body and a surface,
wherein the pressure-mitigation device includes a plurality of chambers, and
wherein the egress interface has a plurality of outlets, each of which is associated with a different chan- nel of the multi-channel tubing through which fluid is able to flow into a corresponding one of the plurality of chambers;

a plurality of transducers housed inside the structural body that are configured to generate a plurality of electrical signals, wherein each electrical signal is representative of a rate at which fluid is flowing into a corresponding chamber of the pressure-mitigation device through a corresponding one of the plurality of outlets along the egress interface to maintain a desired inflation pressure;

a processor; and a memory that includes instructions for determining the health of the human body positioned on the pressure-mitigation device, wherein the instructions, when executed by the processor, cause the controller to:

obtain the plurality of electrical signals that indicate, for each chamber of the pressure-mitigation device, inflation pressure over an interval of time, continually estimate a value of a characteristic of the human body over the interval of time by examining the plurality of electrical signals to identify changes that are indicative of movements of the human body, and inferring the value of the characteristic based on the movements of the human body, and cause display of the value of the characteristic.

2. The controller of claim 1, further comprising:
a display that is configured to present an interface that includes the value of the characteristic.

3. The controller of claim 1, wherein said causing comprises:
transmitting the value to a piece of healthcare equipment that displays the value of the characteristic.

4. The controller of claim 1, wherein the instructions further cause the controller to:
continually compare the value of the characteristic to a predetermined threshold, and
generate a notification responsive to a determination that a given value corresponding to a given point in time exceeds the predetermined threshold.

5. The controller of claim 1, wherein the instructions further cause the controller to:
continually estimate a value of a second characteristic of the human body over the interval of time based on the plurality of electrical signals, and
cause display of the value of second characteristic.

6. The controller of claim 1, wherein the instructions further cause the controller to:
periodically estimate a value of a second characteristic of the human body over the interval of time based on the plurality of electrical signals, and
cause display of the value of the second characteristic.

7. A method performed by a controller that is fluidically coupled to a pressure-mitigation device disposed between a human body and a surface, the method comprising:
obtaining, by the controller, an electrical signal that is generated by a transducer mounted in the controller over an interval of time,
wherein the electrical signal is representative of a rate at which fluid is flowing into a chamber of the pressure-mitigation device through an egress interface of the controller;

examining, by the controller, the electrical signal to identify changes that are indicative of movements of the human body; and estimating, by the controller, a value of a characteristic of the human body based on the movements of the human body, as identified through examination of the electrical signal generated by the transducer.

8. The method of claim 7,
wherein the transducer is one of a plurality of transducers mounted in the controller, and
wherein the controller obtains a plurality of electrical signals generated by the plurality of transducers over the interval of time, each electrical signal being generated by a corresponding transducer based on the inflation pressure of a corresponding chamber of the pressure-mitigation device.

9. The method of claim 7, wherein the characteristic is weight, blood pressure, respiration rate, or heart rate.

10. The method of claim 7, wherein said obtaining, said examining, and said estimating are performed in real time so as to continually establish the value of the characteristic of the human body.

11. The method of claim 7, wherein said obtaining, said examining, and said estimating are performed on an ad hoc basis so as to periodically establish the value of the characteristic of the human body.

12. The method of claim 7, further comprising:
transmitting, by the controller, information related to the characteristic to a destination across a network.

13. The method of claim 12, wherein the destination is a piece of healthcare equipment situated in a healthcare facility.

14. The method of claim 12, wherein the destination is a computing device that is associated with a caregiver responsible for managing the human body.

15. A non-transitory medium with instructions stored thereon that, when executed by a processor, cause the processor to perform operations comprising:
obtaining data that includes a temporal series of values indicative of inflation pressure of each chamber of multiple chambers of a pressure-mitigation device deployed beneath a user over an interval of time, wherein the inflation pressure of each chamber is determined through analysis of a rate at which fluid flows into the chamber;
identifying a computer-implemented model that is trained to identify seizures using patterns of values known to correspond to confirmed instances of seizures experienced by other individuals;
applying the computer-implemented model to the data to discover a pattern of values, in the temporal series of values, that is indicative of a seizure; and
generating a notification that specifies the user experienced a seizure based on the discovery of the pattern of values.

16. The non-transitory medium of claim 15, wherein the processor is contained in a controller that is responsible for controlling inflation of the multiple chambers of the pressure-mitigation device.

17. The non-transitory medium of claim 15, wherein the processor is contained in a computing device that is associated with a caregiver responsible for managing the user.

18. The non-transitory medium of claim 15, wherein the notification is an audible notification or a visual notification generated by a controller that is responsible for controlling inflation of the multiple chambers of the pressure-mitigation device.

19. The non-transitory medium of claim 15, wherein the operations further comprise:
causing transmission of the notification to a computing device that is associated with a caregiver responsible for managing the user.

* * * * *